US011272854B1

(12) United States Patent
Tansley et al.

(10) Patent No.: US 11,272,854 B1
(45) Date of Patent: Mar. 15, 2022

(54) NOISE CANCELLATION IN IMPEDANCE MEASUREMENT CIRCUITS

(71) Applicant: Analog Devices International Unlimited Company, Limerick (IE)

(72) Inventors: Thomas J. Tansley, Andover, MA (US); Colin G. Lyden, Baltimore (IE); Oliver J. Brennan, Oakland, CA (US)

(73) Assignee: Analog Devices International Unlimited Company, Limerick (IE)

( * ) Notice: Subject to any disclaimer, the term of this patent is extended or adjusted under 35 U.S.C. 154(b) by 0 days.

(21) Appl. No.: 17/010,185

(22) Filed: Sep. 2, 2020

(51) Int. Cl.
*A61B 5/053* (2021.01)
*A61B 5/00* (2006.01)
*G01R 27/02* (2006.01)

(52) U.S. Cl.
CPC .......... *A61B 5/053* (2013.01); *A61B 5/7203* (2013.01); *G01R 27/02* (2013.01)

(58) Field of Classification Search
CPC ........ A61B 5/053; A61B 5/7203; G01R 27/02
(Continued)

(56) References Cited

U.S. PATENT DOCUMENTS

| 6,172,483 B1 | 1/2001 | Champlin |
| 7,161,358 B1 | 1/2007 | Tanbakuchi et al. |

(Continued)

FOREIGN PATENT DOCUMENTS

| CN | 105319445 B | 11/2018 |
| CN | 109381180 A | 2/2019 |
| KR | 102118288 B1 | 6/2020 |

OTHER PUBLICATIONS

"PGA302 Sensor Signal Conditioner With 0-5V Ratiometric Output", Texas Instruments Data Sheet, SLDS216, (Dec. 2017), 78 pgs.
(Continued)

*Primary Examiner* — Giovanni Astacio-Oquendo
(74) *Attorney, Agent, or Firm* — Schwegman Lundberg & Woessner, P.A.

(57) ABSTRACT

The present disclosure provides an impedance measurement circuit for measuring and detecting variations in an impedance under test, and methods of operating the impedance measurement circuit. The impedance measurement circuit comprises a plurality of converts, including at least two digital-to-analog converters (DACs). The DACs together alternate between a first mode of operation and a second mode of operation. In the first mode, a first one of the DACs is operational to convert a first digital input signal to a first analog output using a first hardware component, and a second one of the DACs is operational to convert a second digital input signal to a second analog output using a second hardware component. In the second mode, the first one of the DACs is operational to convert the first digital input signal to the first analog output using the second hardware component, and the second one of the DACs is operational to convert the second digital input signal to the second analog output using the first hardware component. By alternating between the first and second modes, the first and the second hardware components are alternately used in the first DAC and the second DAC to perform the respective DAC's conversion operations. Each hardware component may be associated with an intrinsic noise power that causes magnitude errors in the respective DAC's output. Furthermore, the DACs may be arranged such that magnitude errors in the first DAC and magnitude errors in the second DAC cause opposing errors in the impedance measurement made by the impedance measurement circuit. Therefore, by alternating between the first and the second modes, errors in the impedance measurements performed by the impedance measurement circuit are stabilised, or ratiometrically cancelled, over time.

20 Claims, 16 Drawing Sheets

(58) Field of Classification Search
USPC .................................. 324/608, 605, 602, 600
See application file for complete search history.

(56) References Cited

U.S. PATENT DOCUMENTS

| | | | |
|---|---|---|---|
| 7,457,660 | B2 | 11/2008 | Smith et al. |
| 7,504,973 | B2 | 3/2009 | Inagaki |
| 8,031,098 | B1 | 10/2011 | Ebner et al. |
| 9,191,025 | B1 | 11/2015 | Chopra |
| 9,357,944 | B2 | 6/2016 | Lyden et al. |
| 9,817,035 | B2 | 11/2017 | Ogawa et al. |
| 9,825,645 | B1 | 11/2017 | Gaggl et al. |
| 9,980,662 | B2 | 5/2018 | Bibian et al. |
| 10,027,447 | B2 | 7/2018 | Manganaro |
| 10,075,178 | B1 | 9/2018 | Yang |
| 10,075,179 | B1 | 9/2018 | Keane et al. |
| 10,120,005 | B2 | 11/2018 | Cherkassky et al. |
| 2007/0194813 | A1 | 8/2007 | Washburn et al. |
| 2009/0066392 | A1 | 3/2009 | Grosjean et al. |
| 2014/0002133 | A1 | 1/2014 | Daigle et al. |
| 2017/0071552 | A1 | 3/2017 | Harpe et al. |
| 2019/0110694 | A1* | 4/2019 | Jian ........................ A61B 5/022 |
| 2019/0207616 | A1 | 7/2019 | Chen et al. |
| 2019/0383760 | A1 | 12/2019 | Kim |
| 2020/0113523 | A1 | 4/2020 | Osypka et al. |
| 2020/0355732 | A1* | 11/2020 | Koch ..................... G01R 27/26 |
| 2021/0052026 | A1* | 2/2021 | Albaugh ............. A61B 5/0295 |

OTHER PUBLICATIONS

Kusche, R, et al., "Design, Development and Comparison of two Different Measurement Devices for Time-Resolved Determination of Phase Shifts of Bioimpedances", arXiv preprint, arXiv:2008. 02469v1 [physics.ins-det], (Aug. 6, 2020), 4 pgs.

Li, Hui, et al., "A High Accuracy and High Sensitivity System Architecture for Electrical Impedance Tomography System", Pacific Conference on Circuits and Systems (APCCAS), (Oct. 2018), 4 pgs.

McEwan, A, et al., "A review of errors in multi-frequency EIT instrumentation", Physiological measurement, 28(7), S197, (Jun. 2007), 198 pgs.

Mohamadou, Youssoufa, et al., "Performance Evaluation of Wideband Bio-Impedance Spectroscopy Using Constant Voltage Source and Constant Current Source", Measurement Science and Technology, 23(10), 105703, (Sep. 2012), 10 pgs.

"European Application Serial No. 21193664.6, Extended European Search Report dated Dec. 21, 2021", 7 pgs.

Gervasoni, G, et al., "Switched ratiometric lock-in amplifier enabling sub-ppm measurements in a wide frequency range", Review of Scientific Instruments, American Institute of Physics, 2 Huntington Quadrangle, Melville, NY 11747, vol. 88, No. 10, (Oct. 20, 2017), 39 pgs.

* cited by examiner

NOISE CANCELLATION IN IMPEDANCE MEASUREMENT CIRCUITS

TECHNICAL FIELD

The present disclosure relates to an impedance measurement circuit. In particular, the present disclosure relates to a method and an apparatus for reducing noise in an impedance measurement circuit.

BACKGROUND

Impedance measurement circuits are used in a variety of applications to detect variations in an impedance of interest. Impedance measurement circuits are often used in clinical settings to determine physiological parameters of a subject based on detected variations in a bioimpedance. As one example, an impedance measurement circuit can be used to detect variations in a thoracic impedance of a human subject. The thoracic impedance may vary as the subject breathes, and therefore by detecting variations in the thoracic impedance one can infer that the subject is breathing. The thoracic impedance can be used to detect conditions such as sleep apnoea. For example, if variations in the thoracic impedance have not been detected over a period of time, it can be inferred that the subject was not breathing over that period of time, and therefore may be suffering from sleep apnoea.

Impedance measurement circuits include a variety of components including digital to analog converters (DACs) and analog to digital converters (ADCs). Noise properties of the DACs and/or ADCs in the circuit can lead the impedance measurement circuit to falsely detect variations in the impedance. Therefore, this can impact the circuit's ability to accurately infer information from the impedance being measured. As such, in the above given example, noise properties of the circuit can lead to a false inference from the thoracic impedance that the subject is breathing, and therefore conditions such as sleep apnoea are overlooked.

SUMMARY OF THE DISCLOSURE

The present disclosure provides an impedance measurement circuit for measuring and detecting variations in an impedance under test, and methods of operating the impedance measurement circuit. The impedance measurement circuit comprises a plurality of converts, including at least two digital-to-analog converters (DACs). The DACs together alternate between a first mode of operation and a second mode of operation. In the first mode, a first one of the DACs is operational to convert a first digital input signal to a first analog output using a first hardware component, and a second one of the DACs is operational to convert a second digital input signal to a second analog output using a second hardware component. In the second mode, the first one of the DACs is operational to convert the first digital input signal to the first analog output using the second hardware component, and the second one of the DACs is operational to convert the second digital input signal to the second analog output using the first hardware component. By alternating between the first and second modes, the first and the second hardware components are alternately used in the first DAC and the second DAC to perform the respective DAC's conversion operations. Each hardware component may be associated with an intrinsic noise power that causes magnitude errors in the respective DAC's output. Furthermore, the DACs may be arranged such that magnitude errors in the first DAC and magnitude errors in the second DAC cause opposing errors in the impedance measurement made by the impedance measurement circuit. Therefore, by alternating between the first and the second modes, errors in the impedance measurements performed by the impedance measurement circuit are stabilised, or ratiometrically cancelled, over time.

In a first aspect of the present disclosure, there is provided an impedance measurement apparatus comprising a first hardware circuit element and a second hardware circuit element. The apparatus includes a first DAC arranged to convert a first digital input to a first output signal using the first or the second hardware circuit elements. The apparatus further includes a second DAC arranged to convert a second digital input to a second output signal using the first or the second hardware circuit elements. The apparatus is configured to operate in: a first mode in which the first DAC converts the first digital input using the first hardware circuit element and the second DAC converts the second digital input using the second hardware circuit element, and a second mode in which the first DAC converts the first digital input using the second hardware circuit element and the second DAC converts the second digital input using the first hardware circuit element.

In a second aspect of the present disclosure, there is provided a method of ratiometrically cancelling gain errors in an impedance measurement apparatus having a first DAC and a second DAC. The method comprises operating the first DAC and the second DAC in a first mode, in which the first DAC converts a first digital input to a respective first output signal using a first hardware circuit element, and the second DAC converts a second digital input to a second output signal using a second hardware circuit element. The method further comprises operating the first DAC and the second DAC in a second mode in which the first DAC converts the first digital input to the respective first output signal using the second hardware circuit element, and the second DAC converts the second digital input to the second output signal using the first hardware circuit element.

In a third aspect of the present disclosure, there is provided an impedance measurement apparatus comprising a first DAC comprising a first output, wherein the first DAC is configured to convert a first digital input to a first output signal by steering current from a first current source to the first output based on the first digital input. The apparatus further comprises a second DAC comprising a second output, the second DAC configured to convert a second digital input to a second output signal by steering current from a second current source to the second output based on the second digital input. Furthermore, the apparatus comprises a bias circuit configured to bias both the first and the second current sources.

A numbered list of illustrative non-limiting examples is presented by way of overview below.

Example 1 includes an impedance measurement apparatus comprising: a first hardware circuit element and a second hardware circuit element; a first DAC arranged to convert a first digital input to a first output signal using the first or the second hardware circuit elements; and a second DAC arranged to convert a second digital input to a second output signal using the first or the second hardware circuit elements, wherein the apparatus is configured to operate in: a first mode in which the first DAC converts the first digital input using the first hardware circuit element and the second DAC converts the second digital input using the second hardware circuit element, and a second mode in which the first DAC converts the first digital input using the second hardware circuit element and the second DAC converts the second digital input using the first hardware circuit element.

Example 2 can include the apparatus of example 1, wherein the apparatus is configured to alternate between the first mode and the second mode.

Example 3 can include the apparatus of Example 2, wherein the apparatus is configured to alternate between the first mode and the second mode independently of the first and second digital inputs.

Example 4 can include the apparatus of Example 3, wherein the apparatus is configured to alternate between the first and second modes randomly or in a predetermined pattern.

Example 5 can include the apparatus of any of preceding example, wherein the first hardware circuit element and the second hardware circuit element are of the same type.

Example 6 can include the apparatus of any of preceding example, wherein the first hardware circuit element is a first current source, and the second hardware circuit element is a second current source.

Example 7 can include the apparatus of Example 6, wherein the first DAC is configured to steer current from the first or the second current source to a first DAC output depending on the first digital input, and wherein the second DAC is configured to steer current from the first or the second current source to a second DAC output depending on the second digital input.

Example 8 can include the apparatus of Examples 6 or 7, further comprising a plurality of switchable paths arranged to: in the first mode, supply current from the first current source to the first DAC and from the second current source to the second DAC; and in the second mode, supply current from the second current source to the first DAC and from the first current source to the second DAC.

Example 9 can include the apparatus of Examples 6, 7 or 8, further comprising a biasing circuit configured to bias the first and the second current sources.

Example 10 can include the apparatus of an of Examples 1 to 4, wherein the first hardware circuit element is a first bias circuit arranged to bias a first current source of the first DAC or a second current source of the second DAC, and second hardware circuit element is a second bias circuit arranged to bias the first current source or the second current source.

Example 11 can include the apparatus of Example 10, wherein the apparatus is configured such that: in the first mode, the first bias circuit biases the first current source and the second bias circuit biases the second current source; and in the second mode, the first bias circuit biases the second current source and the second bias circuit biases the first current source.

Example 12 can include the apparatus of any preceding example, further comprising: an excitation circuit for outputting an excitation signal to an impedance under measurement, the excitation circuit comprising the first DAC; and a sensing circuit arranged to sense a signal across the impedance, the sensing circuit comprising the second DAC.

Example 13 can include a method of ratiometrically cancelling gain errors in an impedance measurement apparatus having a first DAC and a second DAC, comprising: operating the first DAC and the second DAC in a first mode, in which the first DAC converts a first digital input to a respective first output signal using a first hardware circuit element, and the second DAC converts a second digital input to a second output signal using a second hardware circuit element; operating the first DAC and the second DAC in a second mode in which the first DAC converts the first digital input to the respective first output signal using the second hardware circuit element, and the second DAC converts the second digital input to the second output signal using the first hardware circuit element.

Example 14 can include the method of Example 13, further comprising alternating between the first and second modes of operation.

Example 15 can include the method of Example 14, wherein the first and second modes alternate independently of the digital inputs.

Example 16 can include the method of any of Examples 13 to 16, comprising alternating between the first and second modes randomly or in a predetermined pattern.

Example 17 can include the method of any of Examples 13 to 16, wherein the first hardware circuit element is a first current source, and the second hardware circuit element is a second current source, and wherein: in the first mode the first DAC converts the first digital input by steering current from the first current source to a first DAC output depending on the first digital input, and the second DAC converts the second digital input by steering current from the second current source to a second DAC output depending on the second digital input; and in the second mode the first DAC converts the first digital input by steering current from the second current source to a first DAC output depending on the first digital input, and the second DAC converts the second digital input by steering current from the first current source to a second DAC output depending on the second digital input.

Example 18 can include the method of any of Examples 13 to 16, wherein the first hardware circuit element is a first bias circuit, and the second hardware circuit element is a second bias circuit, wherein: in the first mode the first DAC converts the first digital input using a current source biased by the first bias circuit, and the second DAC converts the second digital input using a current source biased by the second bias circuit; and in the second mode the first DAC converts the first digital input using a current source biased by the second bias circuit, and the second DAC converts the second digital input using a current source biased by the first bias circuit.

Example 19 can include the method of any of Examples 13 to 18, wherein the first DAC is comprised in an excitation circuit for outputting an excitation signal to a bioimpedance, and the second DAC is in a sensing circuit arranged to sense a signal across a bioimpedance.

Example 20 can include an impedance measurement apparatus comprising: a first DAC comprising a first output, wherein the first DAC is configured to convert a first digital input to a first output signal by steering current from a first current source to the first output based on the first digital input, a second DAC comprising a second output, the second DAC configured to convert a second digital input to a second output signal by steering current from a second current source to the second output based on the second digital input, and a bias circuit configured to bias the first and the second current source.

BRIEF DESCRIPTION OF THE DRAWINGS

Examples of the present disclosure are now described with reference to the accompanying drawings, in which.

DETAILED DESCRIPTION

Figure 1:
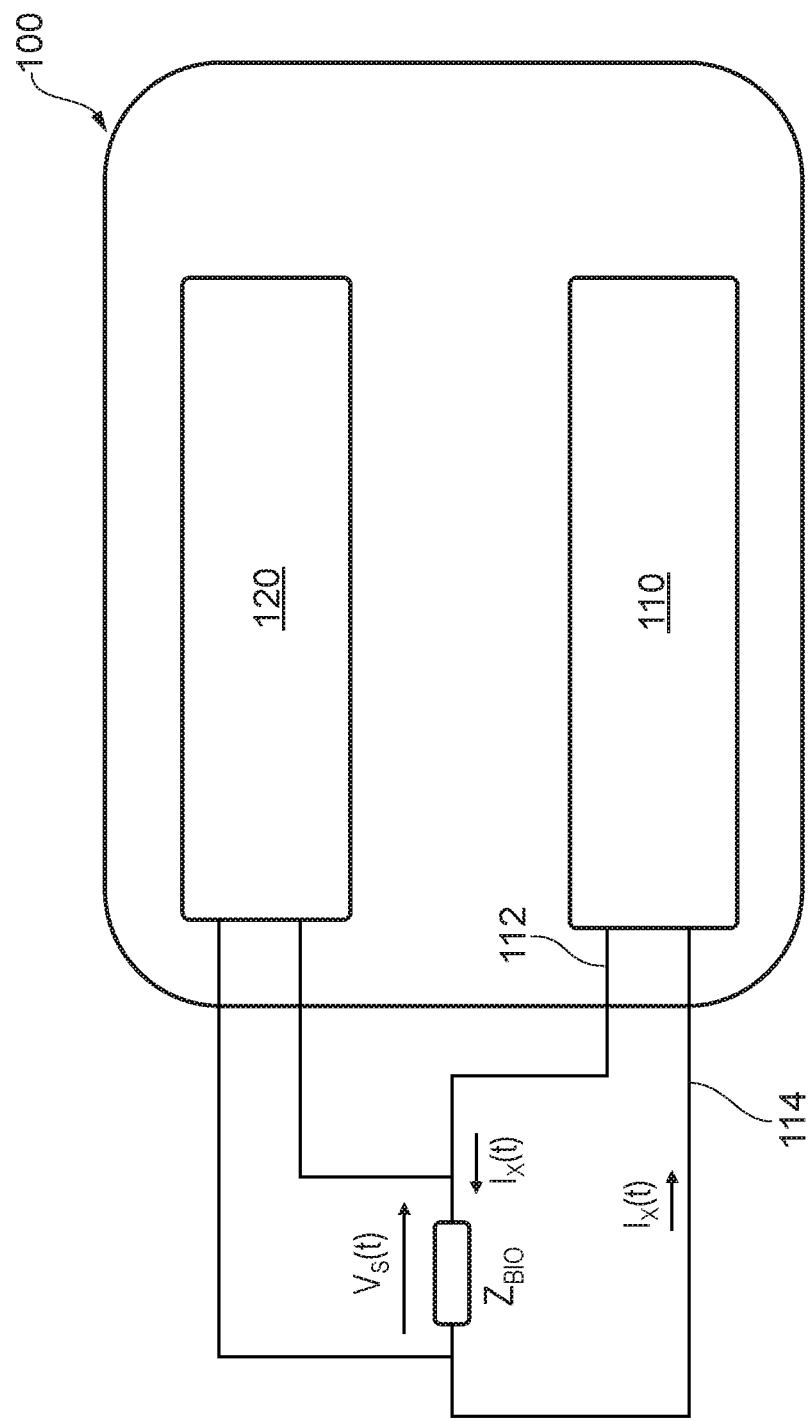
FIG. 1 shows an impedance measurement circuit according to an example of the present disclosure.

The present disclosure relates to an impedance measurement circuit. In particular, the disclosure relates to methods and circuit arrangements for reducing the effects of hardware intrinsic noise in the impedance measurement circuit.

An impedance measurement circuit may include an excitation DAC that excites an impedance with a carrier signal, such as a 50 kHz sinewave. The carrier signal is typically a current signal. A sensing ADC then senses a voltage signal across the impedance. The ADC converts the sensed voltage signal to a sensed digital signal. The impedance measurement circuit analyses the sensed digital signal to detect variations in the impedance. The sensed digital signal may include a frequency component at 50 kHz according to the frequency of the carrier signal. The sensed digital signal may also include an additional frequency component corresponding to the frequency of variations in the impedance. In one application, the impedance may be a thoracic impedance of a human subject, which varies as the subject breathes. Therefore, the additional frequency component may be much lower at approximately 0.3 Hz, caused by slow variations in the impedance. The sensed digital signal can be analysed to detect the 0.3 Hz component, and therefore determine if the subject is breathing.

One problem with such circuits is that noise from circuit components of the excitation DAC can impact how the excitation DAC generates the carrier signal. This may cause errors in the magnitude of the carrier signal. Furthermore, noise from circuit components of the feedback DAC can impact how the ADC converts the sensed voltage signal to the sensed digital signal, which may cause errors in the magnitude of the sensed digital signal. Overall, both types of error may be compounded and cause a time-varying magnitude error in the sensed digital signal. The time-varying error will vary at a low frequency, e.g. close to 0.3 Hz. Therefore, even when the impedance is not varying, the impedance measurement circuit may detect the error frequency component that looks like the frequency component of the impedance, and falsely determine that the impedance is varying. If the impedance is a thoracic impedance as described above, this can cause the impedance measurement circuit to falsely detect breathing and conditions such as sleep apnoea may be overlooked.

The present disclosure proposes to average out or "ratiometrically cancel" the time-varying errors over time, by swapping and/or sharing components between the excitation DAC and the feedback DAC. In particular, the inventors have identified that a noisy component used in the excitation DAC to generate the carrier signal, will have an opposite error effect on the sensed digital signal compared to when the same noisy component is used in the feedback DAC of the ADC. Similarly, a noisy component originally used in the feedback DAC, will have an opposite error effect on the sensed digital signal compared to when the same noisy component is used in the excitation DAC. Therefore, by swapping the noisy components between the excitation DAC and the feedback DAC back and forth over time, the magnitude errors in the sensed digital signal can be stabilised, and the error frequency component of the sensed digital signal can be suppressed. Furthermore, sharing some of the noisy components may reduce the total amount of noise in the impedance measurement circuit and further reduce the magnitude errors.

Typically, the excitation DAC and the feedback DAC contain respective sets of current sources for generating their respective outputs. Furthermore, each DAC typically contains at least one respective bias circuit for setting the current level of that DAC's current sources. However, the current sources and the bias circuits can be noisy components as explained above. Therefore, in one example, the impedance measurement circuit can include a circuit arrangement to swap current sources of the excitation DAC with respective current sources of the feedback DAC, back and forth over time. As such, a current source of the excitation DAC and a respective current source of the feedback DAC may be seen to operate in: a first mode in which the current source of the excitation DAC is used in the excitation DAC to generate the carrier signal and the current source of the feedback DAC is used in the feedback DAC as part of the ADC function; and a second mode in which the current source originally from the excitation DAC is now used in the feedback DAC as part of the ADC function and the current source originally from the feedback DAC is now used in the excitation DAC to generate the carrier signal.

In a further example, the impedance measurement circuit can include a circuit arrangement to swap the bias circuit of the excitation DAC with the bias circuit of the feedback DAC, back and forth over time. As such, the bias circuits may be seen to operate in: a first mode in which the bias circuit of the excitation DAC is used in the excitation DAC to set the currents of the excitation DAC's current sources and the bias circuit of the feedback DAC is used in the feedback DAC to set the currents of the feedback DAC's current sources; and a second mode in which the bias circuit originally from the excitation DAC is used in the feedback DAC to set the currents of the feedback DAC's current sources and the bias circuit originally from the feedback DAC is used in the excitation DAC to set the currents of the excitation DAC's current sources.

In an alternative example, the excitation DAC and the feedback DAC may instead share the same bias circuit, such that the same bias circuit sets the currents of the current sources of both the excitation DAC and the feedback DAC.

Impedance Measurement Circuit

FIG. 1 illustrates an impedance measurement circuit 100 for measuring an impedance $Z_{BIO}$ and in particular for detecting variations in the impedance $Z_{BIO}$. In example scenario, the impedance $Z_{BIO}$ is a bioimpedance that may correspond to a thoracic impedance of a human subject. The thoracic impedance may change or vary over time as the subject breathes. A typical thoracic impedance may be approximately 1k Ohms. As the subject breathes, the thoracic impedance can be expected to periodically vary at a frequency of approximately $F_{BIO}$=0.3 Hz, with a change in magnitude of about 1 Ohm. In such scenarios, it is desirable to detect variations in the bioimpedance $Z_{BIO}$, to determine whether the patient is breathing.

The impedance measurement circuit 100 comprises an excitation circuit 110 and a sensing circuit 120. The excitation circuit 110 is configured to generate and output an excitation current signal $I_X(t)$ to the bioimpedance $Z_{BIO}$. In particular, the excitation circuit 110 provides the current signal $I_X(t)$ to the bioimpedance $Z_{BIO}$ via a first current path 112, and returns the current signal $I_X(t)$ via a second current path 114. Preferably, the current signal $I_X(t)$ is a time varying AC sinewave. In the example scenario, the current signal $I_X(t)$ may have frequency of $F_C$=50 kHz. However, it should be appreciated that different types of excitation signal of different shape and/or frequency $F_C$ may be used depending on the type of impedance $Z_{BIO}$ being measured.

By exciting the bioimpedance $Z_{BIO}$ with the excitation current signal $I_X(t)$, a voltage signal $V_S(t)$ is induced across the bioimpedance $Z_{BIO}$. The voltage signal $V_S(t)$ will also be a time varying AC signal having a frequency of $F_C$=50 KHz, in correspondence with the excitation signal $I_X(t)$. However, if the bioimpedance $Z_{BIO}$ is varying at the frequency $F_{BIO}$, this will further modulate the voltage signal $V_S(t)$ by the frequency $F_{BIO}$. Since $F_{BIO}$ is significantly smaller than $F_C$, the frequency component $F_C$ is effectively a carrier frequency for the frequency component $F_{BIO}$. Therefore the voltage signal $V_S(t)$ will contain frequency components at $F_C$ and $F_C F_{BIO}$. As such, in the above examples, the voltage signal $V_S(t)$ will contain frequency components at approximately 50 kHz, 50000.3 Hz and 49999.7 Hz.

The sensing circuit 120 is configured to sense the voltage signal $V_S(t)$ across the bioimpedance $Z_{BIO}$. Furthermore, the sensing circuit 120 is configured to detect the presence of the frequency component $F_{BIO}$ in the voltage signal $V_S(t)$. In some examples, the sensing circuit 120 may first demodulate $V_S(t)$ to remove the carrier frequency component $F_C$ before detecting the bioimpedance frequency component $F_{BIO}$. In any case, by detecting the presence of the particular frequency component of interest $F_{BIO}$, the sensing circuit 120 is able to detect variations in $Z_{BIO}$, and therefore whether the subject is breathing.

As will be described in more detail below, noise sources in both the excitation circuit 110 and the sensing circuit 120 can cause the sensing circuit 120 to falsely detect the frequency component $F_{BIO}$, and therefore cause false detections of subject breathing.

Figure 2A:
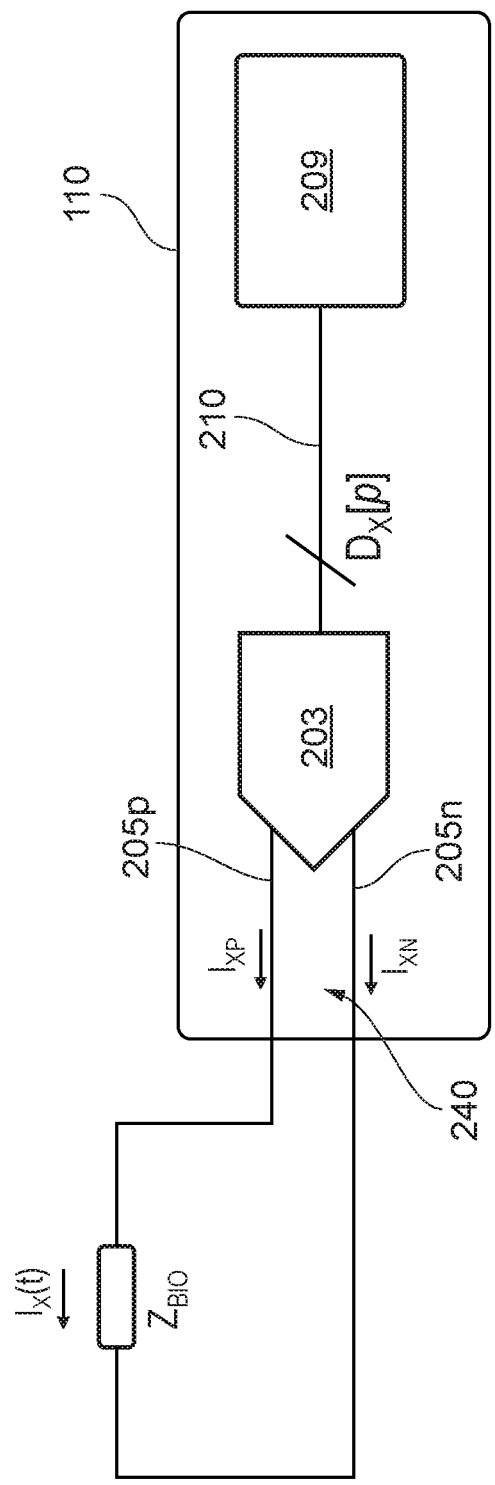
FIG. 2A shows an excitation circuit of the impedance measurement circuit of FIG. 1 according to an example of the present disclosure.

FIG. 2A illustrates an example of the excitation circuit 110 of FIG. 1. The excitation circuit 110 comprises an excitation DAC 203, and a digital signal generator 209. The digital signal generator 209 is coupled to the excitation DAC 203 by a digital signal line 201. The signal generator 209 is configured to generate a N-bit digital signal $D_X[p]$, whereby $p=t/T_X$ and $T_X$ is a clocking period of the signal generator 209 and the excitation DAC 203. The digital signal $D_X[p]$ is a digital representation of the excitation signal $I_X(t)$. In particular, the digital signal $D_X[p]$ may be a digital representation of a sinusoidal signal having a frequency $F_C$=50 kHz, in correspondence with the properties of the analog excitation signal $I_X(t)$ in the above example scenario.

The excitation DAC 203 is arranged to receive the digital signal $D_X[p]$ over the digital signal line 201, and convert the digital signal $D_X[p]$ to the analog excitation signal $I_X(t)$. In particular, the excitation DAC 203 converts instances or values of the digital signal $D_X[p]$ to the analog excitation signal $I_X(t)$ at the clocking frequency $1/T_X$. Preferably, the excitation DAC 203 is a current-steering DAC so that it may output the excitation current signal $I_X(t)$. More preferably, the excitation DAC 203 is a differential current-steering DAC. Therefore, as illustrated in FIG. 2A, the excitation DAC 203 outputs the excitation current signal $I_X(t)$ to a differential output 240. The excitation current signal $I_X(t)$ is formed of a positive part $I_{XP}$ provided to a positive branch 205p of the differential output 240, and a negative part $I_{XN}$ provided to a negative branch 205n of the differential output 240, wherein $I_X(t)=I_{XP}-I_{XN}$. As illustrated in FIG. 2A, each branch 205p and 205n of the differential output 240 may couple to respective sides of the bioimpedance $Z_{BIO}$ in order to provide the excitation signal $I_X(t)$ to the bioimpedance $Z_{BIO}$. Optionally, although not shown in FIG. 2A, the excitation circuit 110 may further comprise a buffer circuit arranged to buffer the output of the excitation DAC 203 before the excitation signal $I_X(t)$ is provided to the bioimpedance $Z_{BIO}$.

Figure 2B:
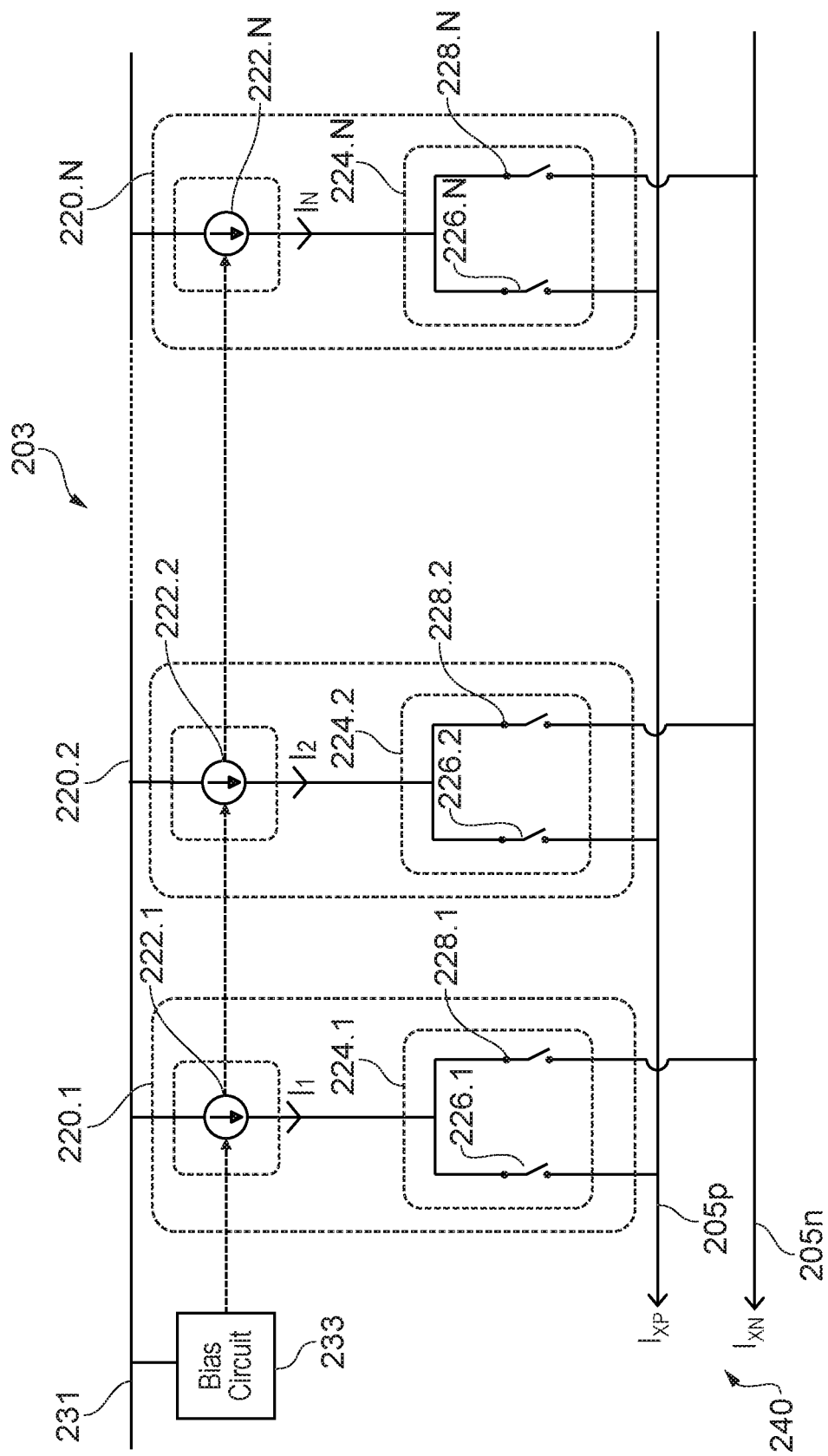
FIG. 2B shows an excitation DAC of the excitation circuit of FIG. 2A, according to an example of the present disclosure.

FIG. 2B illustrates an example of the excitation DAC 203 of FIG. 2A. The excitation DAC 203 comprises a plurality of DAC units 220.1, 220.2, ..., 220.N. Each DAC unit 220.1, 220.2, ..., 220.N is coupled between a power supply rail 231 and the DAC's output 240. Furthermore, each n'th DAC unit 220.n is configured to convert a respective n'th bit $D_X[p]^n$ of the digital signal $D_X[p]$ in order to provide the excitation signal $I_X(t)$, wherein n=1 ... N.

Each n'th DAC unit 220.n comprises a current source 222.n and a current steering circuit 224.n. The current source 222.n is coupled between the power supply rail 231 and the current steering circuit 224.n. The current source 222.n is arranged to supply a current $I_n$ to the current steering circuit 224.n.

The current steering circuit 224.n is arranged to receive the current $I_n$ from the current steering circuit 224.n. The current steering circuit 224.n is configured to steer the current $I_n$ supplied by the current source 222.n to either the positive branch 205p or the negative branch 205n of the DAC's output 240, depending on the value of the respective n'th bit $D_X[p]$ of the digital signal $D_X[p]$. In particular, the current steering circuit 224.n comprises a pair of current steering switches including a first current steering switch 226.n and a second current steering switch 228.n. The first current steering switch 226.n is arranged to switchably couple the output of the current source 222.n to the positive branch 205p of the DAC output. The second current steering switch 228.n is arranged to switchably couple the output of the current source 222.n to the negative branch 205n of the DAC output.

In operation, if $D_X[p]^n$='1' or 'high' for a particular instance p, the current steering circuit 224.n may steer the current $I_n$ to the positive branch 205p of the DAC output 240, by closing the first current steering switch 226.n and opening the second current steering switch 228.n. If $D_X[p]$='0' or 'low' for a particular instance p, the current steering circuit 224.n may steer the current $I_n$ to the negative branch 205n of the DAC output 240, by opening the first current steering switch 226.n and closing the second current steering switch 228.n. As such, the feedback DAC 303 is able to convert a digital signal $D_X[p]$ into an analog output $I_X t$ by appropriately steering the outputs of each of the current sources 222.1 to 222.N to the DAC's output 240.

Although not shown in FIG. 2B, each current steering circuit 224.n may be configured to receive a respective n'th bit $D_X[p]^n$ of the digital signal $D_X[p]$ and control its operation based on the value of that n'th bit $D_X[p]^n$. For example, the current steering switch 226.n may be arranged to receive the n'th bit $D_X[p]^n$ as a control signal such that the current steering switch 226.n is in a closed state when $D_X[p]^n$ is 1 or high, or in an open state when $D_X[p]^n$ is 0 or low. Additionally, the current steering switch 228.n may receive a complement of the n'th bit $D_X[p]^n$ so that it is in an opposite state to the other current steering switch 226.n for each instance of the digital signal.

The excitation DAC 203 further comprises a bias circuit 233. The bias circuit 233 is coupled to the power supply rail 231 and to each of the current sources 222.1, 222.2 ... 222.N. The bias circuit 233 is configured to bias each of the current sources 222.1, 222.2 ... 222.N. Preferably, the bias circuit 233 biases each of the current sources, so that each current source outputs substantially the same current, such that $I_1=I_2=I_N$. However, in other examples, the current sources may be binary weighted such that $I_1=2^0*I_1$, $I_2=2^1*I_1$, ... $I_N=2^{N-1}*I_1$.

Figure 3A:
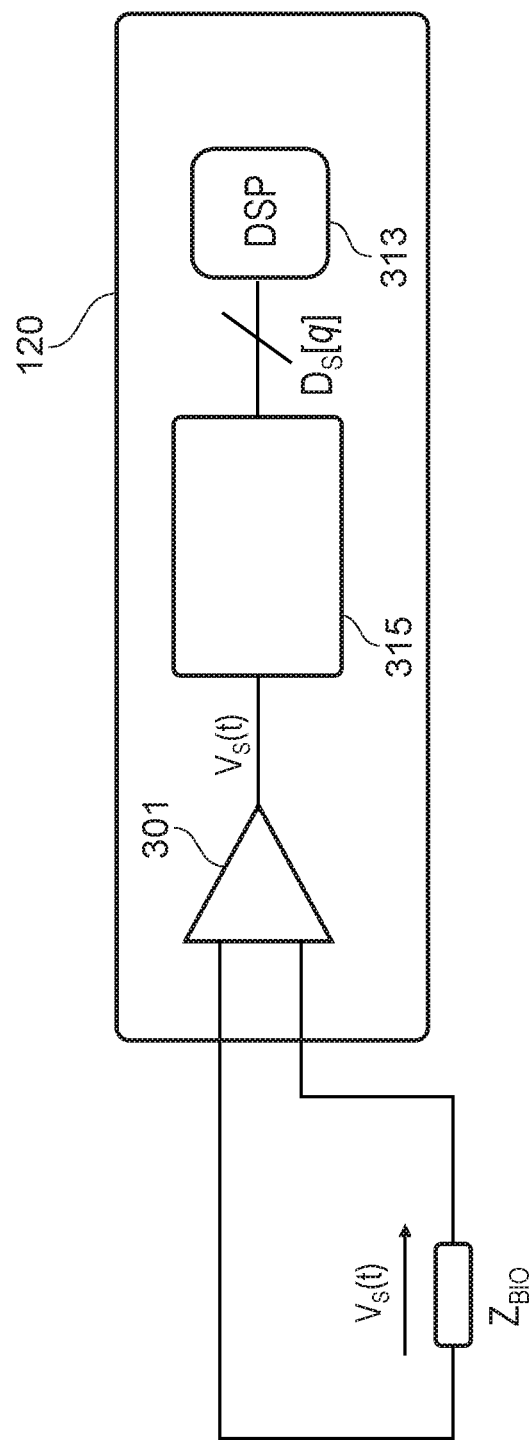
FIG. 3A shows a sensing circuit of the impedance measurement circuit of FIG. 1, according to an example of the present disclosure.

FIG. 3A illustrates an example of the sensing circuit 120 of FIG. 1. The sensing circuit 120 comprises an input buffer 301, an analog to digital converter (ADC) 315 and a digital signal processor (DSP) 313. The input buffer 301 is arranged to receive the voltage signal $V_S(t)$ and provide the voltage signal $V_S(t)$ to the ADC 315. The ADC 315 is configured to convert the voltage signal $V_S(t)$ to a M-bit digital representation of the voltage signal, denoted as $D_S[q]$, wherein q is an integer, $q=t/T_S$ and $T_S$ is a sampling frequency of the ADC 315. The ADC 315 is arranged to output the digital signal $D_S[q]$ to the DSP 313. The DSP 313 is configured to analyse the digital signal $D_S[q]$ to detect variations in the bioimpedance $Z_{BIO}$. For example, the DSP 313 may be configured to detect the frequency of interest $F_{BIO}$ amongst other frequencies of interest, as explained above. In some examples, the DSP 313 is also configured to digitally demodulate the digital signal $D_S[q]$ from the carrier frequency $F_C$ to DC level, before detecting variations in the bioimpedance $Z_{BIO}$.

FIG. 36 illustrates an example of the ADC 315 of FIG. 3A. In the present example, the ADC 315 is a continuous-time sigma delta ADC. The ADC 315 comprises a subtractor 305, a loop filter 307, a quantizer 309 and a feedback DAC 303.

Preferably, the feedback DAC 303 is a current steering DAC, similar to the excitation DAC 203. The feedback DAC 303 is arranged to receive the digital signal $D_S[q]$ from the output of the ADC 315 in a feedback path over a digital signal line 311. The feedback DAC 303 is configured to convert the digital signal $D_S[q]$ into an analog feedback current signal $I_F(t)$. In particular, the feedback DAC 303 converts instances or values of the digital signal $D_S[q]$ to the analog feedback signal $I_F(t)$ at the clocking frequency $1/T_S$. The feedback DAC 303 is configured to output the feedback current signal $I_F(t)$ to an output 340 of the DAC 303.

The subtractor 305 is arranged to subtract the feedback current signal $I_F(t)$ from the voltage signal $V_S(t)$. The subtractor 305 may be configured to first convert the feedback current signal $I_F(t)$ into a corresponding voltage signal $V_F(t)$ before performing the subtraction. Alternatively, the input buffer 301 or the subtractor 305 may be configured to convert the voltage signal $V_S(t)$ to a corresponding current signal $I_S(t)$ before performing the subtraction at the subtractor 305.

The loop filter is configured to filter the output of the subtractor 305. The quantizer 309 is configured to quantize the output of the loop filter and thereby generate the next instance of the digital signal $D_S[q+1]$. It should be appreciated that the continuous time sigma delta ADC 315 may operate as is known in the art, and therefore the operating principles of the ADC 315 have not been described in detail.

Figure 3B:
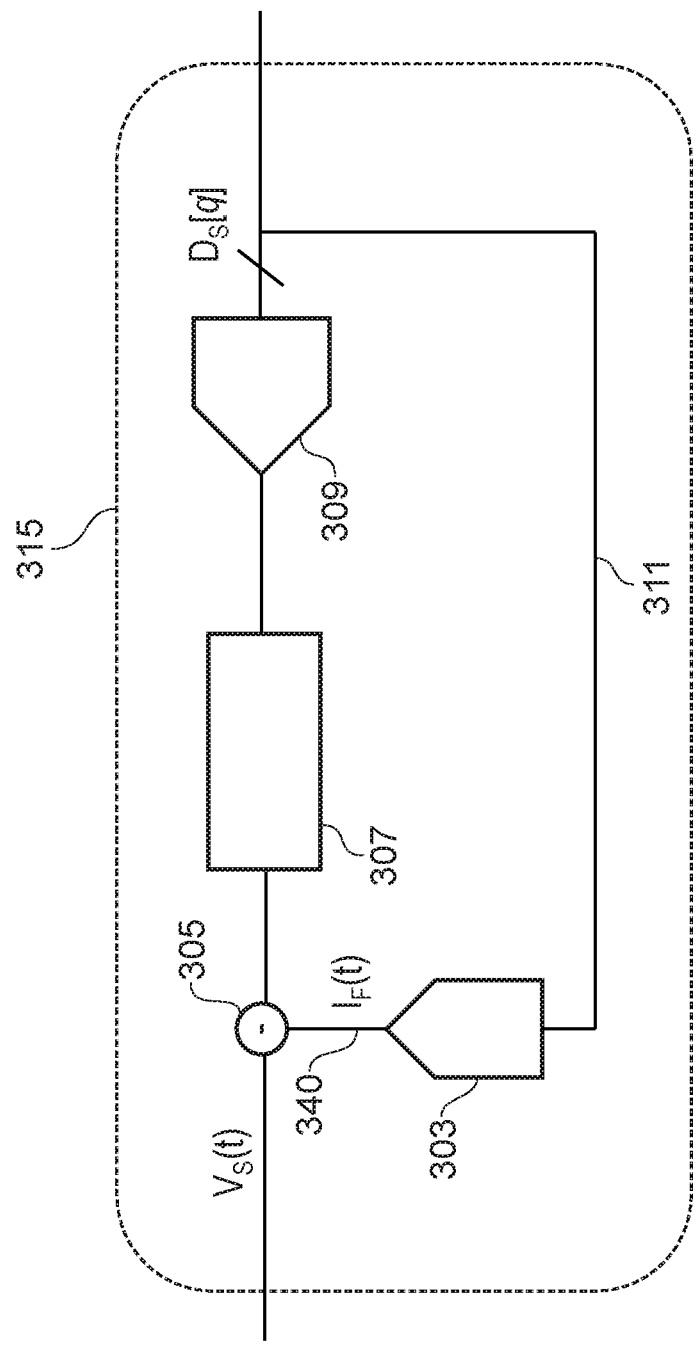
FIG. 3B shows an ADC of the sensing circuit of FIG. 3A, according to an example of the present disclosure.
Figure 3C:
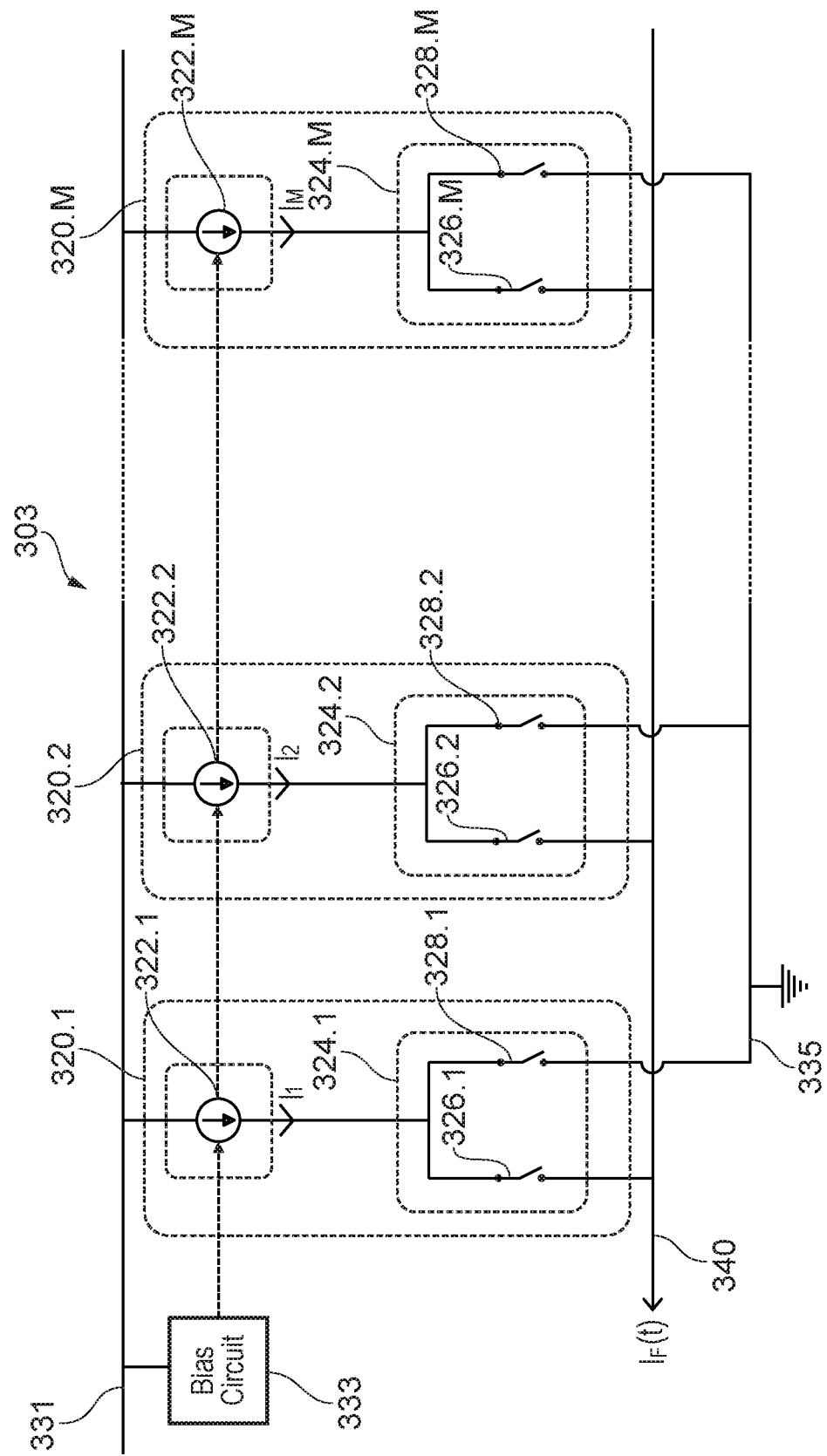
FIG. 3C shows a feedback DAC of the ADC of FIG. 3B according to an example of the present disclosure.

FIG. 3C illustrates an example of the feedback DAC 303 of FIG. 3B. The feedback DAC 303 comprises a plurality of DAC units 320.1, 320.2, ..., 320.M. Each DAC unit 320.1, 320.2, ..., 320.M is coupled between a power supply rail 331, the DAC output 340, and ground 335. Furthermore, each m'th DAC unit 320.m is configured to convert a respective m'th bit $D_S[q]^m$ of the digital signal $D_S[q]$, wherein m=1 ... M.

Each m'th DAC unit 320.m comprises a current source 322.m and a current steering circuit 324.m. The current source 322.m is coupled between the power supply rail 331 and the current steering circuit 324.m. The current source 322.m is arranged to supply a current $I_m$ to the current steering circuit 324.m.

The current steering circuit 324.m is arranged receive the current $I_m$ from the current source 322.m. The current steering circuit 324.m is configured to steer the current $I_m$ supplied by the current source 322.m to either the DAC output 340 or ground 335, depending on the value of the respective m'th bit $D_S[q]^m$ of the digital signal $D_S[q]$. In particular, the current steering circuit 324.m comprises a pair of current steering switches including a first current steering switch 326.m and a second current steering switch 328.m. The first current steering switch 326.m is arranged to switchably couple the output of the current source 322.m to the DAC output 340. The second current steering switch 328.m is arranged to switchably couple the output of the current source 322.m to ground 335.

In operation, if $D_S[q]^m$='1' or 'high', the current steering circuit 324.m may steer the current $I_m$ to the DAC output 340, by closing the first current steering switch 326.m and opening the second current steering switch 328.m. If $D_S[q]^m$='0' or 'low', the current steering circuit 324.m may steer the current $I_m$ to ground by opening the first current steering switch 326.m and closing the second current steering switch 328.m. As such, the feedback DAC 303 is able to convert a digital signal $D_S[q]$ into an analog output $I_F(t)$ by appropriately steering the outputs of each of the current sources 322.1 to 322.M to the output 340.

Although not shown in FIG. 3C, each current steering circuit 324.m may be configured to receive a respective m'th bit $D_S[q]^m$ of the digital signal $D_S[q]$ and control its operation based on the value of that m'th bit $D_S[q]^m$. For example, the current steering switch 326.m may be arranged to receive the m'th bit $D_S[q]^m$ as a control signal such that the current steering switch 326.m is in a closed state when $D_S[q]^m$ is 1 or high, or in an open state when $D_S[q]^m$ is 0 or low. Additionally, the current steering switch 328.m may receive a complement of the n'th bit $D_S[q]^m$ so that it is in an opposite state to the other current steering switch 326.n for each instance of the digital signal.

The feedback DAC 303 further comprises a bias circuit 333. The bias circuit 333 is coupled to the power supply rail 331 and each of the current sources 322.1, 322.2 . . . 322.M. The bias circuit 333 is configured to bias each of the current sources 322.1, 322.2 . . . 322.M. In particular, the bias circuit 333 preferably biases each of the current sources so that each current source outputs substantially the same current, such that $I_1=I_2=\ldots=I_M$. However, in other examples, the current sources may be binary weighted such that $I_1=2^0 I_1$, $I2=2^1 I_1$, $I_M=2^{M-1}I_1$.

In a preferred example of the impedance measurement circuit 100, the digital signals $D_S[q]$ and $D_X[p]$ have the same resolution, and therefore the excitation DAC 203 and the feedback DAC 303 also have the same resolution such that N=M. In other words, the digital signals $D_S[q]$ and $D_X[p]$ have the same number of bits, and therefore the excitation DAC 203 and the feedback DAC 303 are configured to convert the same number of bits such that N=M. In a further preferred example of the impedance measurement circuit, each n'th current source of the excitation DAC 203 is configured and biased to output the same current as each m'th current source corresponding to the same bit. In other words, the current sources are biased such that $I_n=I_m$ for each n=1 to N and m=1 to M and n=m.

Although the feedback DAC 303 is described as providing a single ended output 340, it will be appreciated that the feedback DAC 303 may also be implemented with a differential output, similar to the output of the excitation DAC 203 described above.

System Gain Errors

The digital output $D_S[q]$ of the ADC 315 can be represented as:

$$D_S[q]=G*f(I_X(t),Z_{BIO}), \quad (1)$$

whereby G represents a system gain of the impedance measurement circuit 100, and the function $f(I_X(t), Z_{BIO})$ represents the dependency of $D_S[q]$ on the excitation signal $I_X(t)$ and the value of the impedance $Z_{BIO}$. The system gain G can be defined as:

$$G=I_{ADC}/I_{XDAC}, \quad (2)$$

whereby $I_{ADC}$ represents the full scale current of the ADC 315 of the sensing circuit 120, and $I_{XDAC}$ represents the full scale current of the excitation DAC 203 of the excitation circuit 110. In other words, $I_{ADC}$ may be considered as the largest current achievable by the feedback signal $I_F(t)$ at the output 340 of the feedback DAC 303. Similarly, $I_{XDAC}$ may be considered as the largest current achievable by the excitation signal $I_X(t)$ at the output 240 of the excitation DAC 203. In operation, the output $I_F(t)$ of the feedback DAC 303 is effectively a proportion of the full scale current $I_{ADC}$, controlled by the value of the feedback DAC's 303 digital input $D_S[q]$. Similarly, the output $I_X(t)$ of the excitation DAC 203 is effectively a proportion of the full scale current $I_{XDAC}$, controlled by the value of the digital input $D_X[p]$.

Ideally, the full scale currents $I_{ADC}$ and $I_{XDAC}$ remain constant, and the system gain G remains stable. Therefore, from equation (1), the digital signal $D_S[q]$ should only contain frequency components from the excitation signal $I_X(t)$ and from variations in the bioimpedance $Z_{BIO}$ as explained above.

However, hardware components/elements of the excitation DAC 203 may exhibit intrinsic noise properties. This can cause the excitation DAC's 203 full scale current $I_{XDAC}$ to vary over time. Similarly, hardware components/elements of the feedback DAC 303 may also exhibit intrinsic noise properties. This can also cause the ADC's 315 full scale current $I_{ADC}$ to vary over time.

The variations in $I_{XDAC}$ and $I_{ADC}$ may cause the system gain G to vary at a frequency $F_G$. Therefore, from equation (1), the digital output $D_S[q]$ of the ADC 315 will contain a corresponding time-varying magnitude error caused by noise from both the excitation circuit 110 and the sensing circuit 120. The magnitude error will also vary at the frequency $F_C$. Problematically, the frequency $F_G$ of the magnitude error can be at or close to the frequency of interest $F_{BIO}$, such that $FG \approx F_{BIO}$. Therefore, even when the bioimpedance $Z_{BIO}$ is not varying, the DSP 317 may detect the frequency component $F_G$ in the digital signal $D_S[q]$ corresponding to the frequency of interest $F_{BIO}$. In the above example scenario, this may cause the impedance measurement circuit to falsely detect variations in the thoracic impedance $Z_{BIO}$ and therefore falsely determine that the subject is breathing.

Hardware components of the excitation DAC 203 and feedback DAC 303 that exhibit intrinsic noise may include: the current sources 222.1 . . . 222.N and the bias circuit 233 of the excitation DAC 203, and the current sources 322.1 . . . 322.M and the bias circuit 333 of the feedback DAC 303. Referring to FIG. 2B, each current source 222.1 to 222.N may exhibit hardware intrinsic noise that causes fluctuations in the DAC's full scale current $I_{XDAC}$. For example, each current source may have an intrinsic noise power $P_{XNC}$. Furthermore, the bias circuit 233 may also have an associated noise power that causes fluctuations in the DACs 203 full scale current $I_{XDAC}$. For example, the bias transistor 4330 may have a noise power $P_{XB}$. Since the excitation DAC 203 has N DAC units, the excitation DAC 203 may have a total noise power of $N*P_{XB}+\sqrt{N}*P_{XNC}$. The current sources 322.1 to 322.M and the bias circuit 333 of the feedback DAC 303 may have similar noise properties $P_{SNC}$ and $P_{SB}$, respectively. Therefore, since the feedback DAC 303 has M DAC units, the excitation DAC 203 may have a total noise power of $M*P_{SB}+\sqrt{M}*P_{SNC}$.

Figure 4:
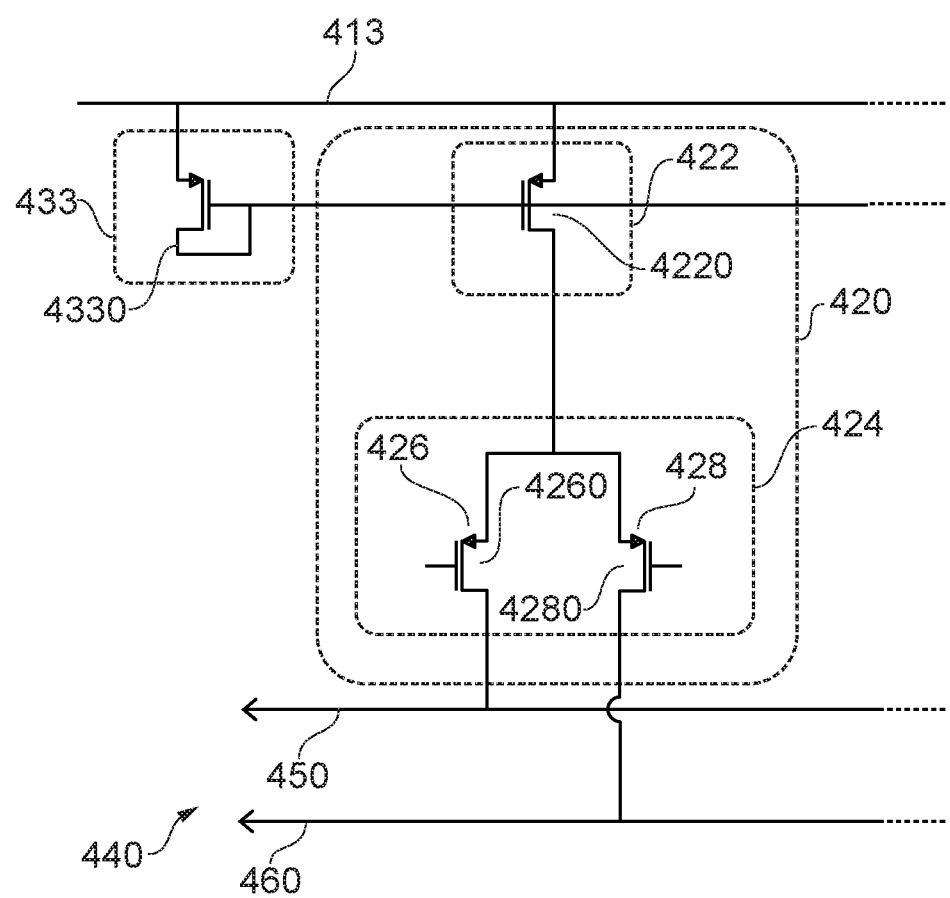
FIG. 4 shows an example implementation of a DAC unit and a bias circuit of the excitation DAC of FIG. 2B and/or the feedback DAC of FIG. 3C.

FIG. 4 illustrates an example implementation of a bias circuit 433 and a DAC unit 420. The DAC unit 420 includes a current source 422 and a current steering circuit 424. The current steering circuit 424 incudes a first current steering switch 426 and a second current steering switch 428.

The DAC unit 420 may be viewed as an example implementation of each DAC unit 220.1 to 220.N from the excitation DAC 203 and each DAC unit 320.1 to 320.M from the feedback DAC 303. Furthermore, the bias circuit 433 may also be viewed as an example implementation of the bias circuit 233 from the excitation DAC 203 and the bias circuit 333 from the feedback DAC 303. Therefore, the DAC unit 420 and the bias circuit 433 may operate as described above in respect to the excitation DAC 203 and the feedback DAC 303, and therefore the operating principles of the DAC unit 420 and the bias circuit 433 are not described in detail.

As shown in FIG. 4, each of the first current steering switch 426, the second current steering switch 428, the current source 422 and the bias circuit 433 are implemented with respective MOS transistors 4260, 4280, 4220 and 4330. In the particular example of FIG. 4, the transistors 4260, 4280, 4220 and 4330 are PMOS transistors. However, it should be appreciated that implementations using NMOS transistors are also possible.

The MOS transistor 4220 of the current source 422 may exhibit hardware intrinsic noise that causes fluctuations in the DAC's full scale current. For example, each current source transistor 4220 may have an intrinsic noise power $P_{NC}$. Furthermore, the MOS transistor 4330 of the bias circuit 433 may also have an associated noise power $P_B$. Hence, for a DAC with N DAC units, the DAC may have a total noise power of $N*P_B + \sqrt{N}*P_{NC}$.

Ratiometric Cancelling of Gain Errors

It can be observed from equations (1) and (2) above that the full scale current $I_{XDAC}$ is inversely proportional to the digital signal $D_S[q]$. Therefore: a positive magnitude error in the full scale current $I_{XDAC}$ will cause a negative error in the system gain G and a negative error in the digital signal $D_S[q]$; and a negative magnitude error in $I_{XDAC}$ will cause a positive error in the system gain G and a positive error in the digital signal $D_S[q]$. On the other hand, the full scale current $I_{ADC}$ is proportional to the digital signal $D_S[q]$, and therefore: a positive magnitude error in the full scale current $I_{ADC}$ will cause a positive error in the system gain G and a positive error in the digital signal $D_S[q]$; and a negative magnitude error in $I_{ADC}$ will cause a negative error in the system gain G and a negative error in the digital signal $D_S[q]$.

The inventors of the present invention have identified that the magnitude errors in the system gain G can be ratiometrically cancelled, by alternately swapping noisy components of the excitation DAC 203 with corresponding noisy components of the feedback DAC 303 at an appropriate speed. Consequently, the system gain G can be stabilised against the varying magnitude errors in $I_{XDAC}$ and $I_{ADC}$. By stabilising the system gain G, the digital signal $D_S[q]$ may no longer contain the frequency component $F_G$ associated with variations in the system gain G, and therefore the chances of falsely detecting variations in $Z_{BIO}$ can be significantly reduced.

Figure 5A:
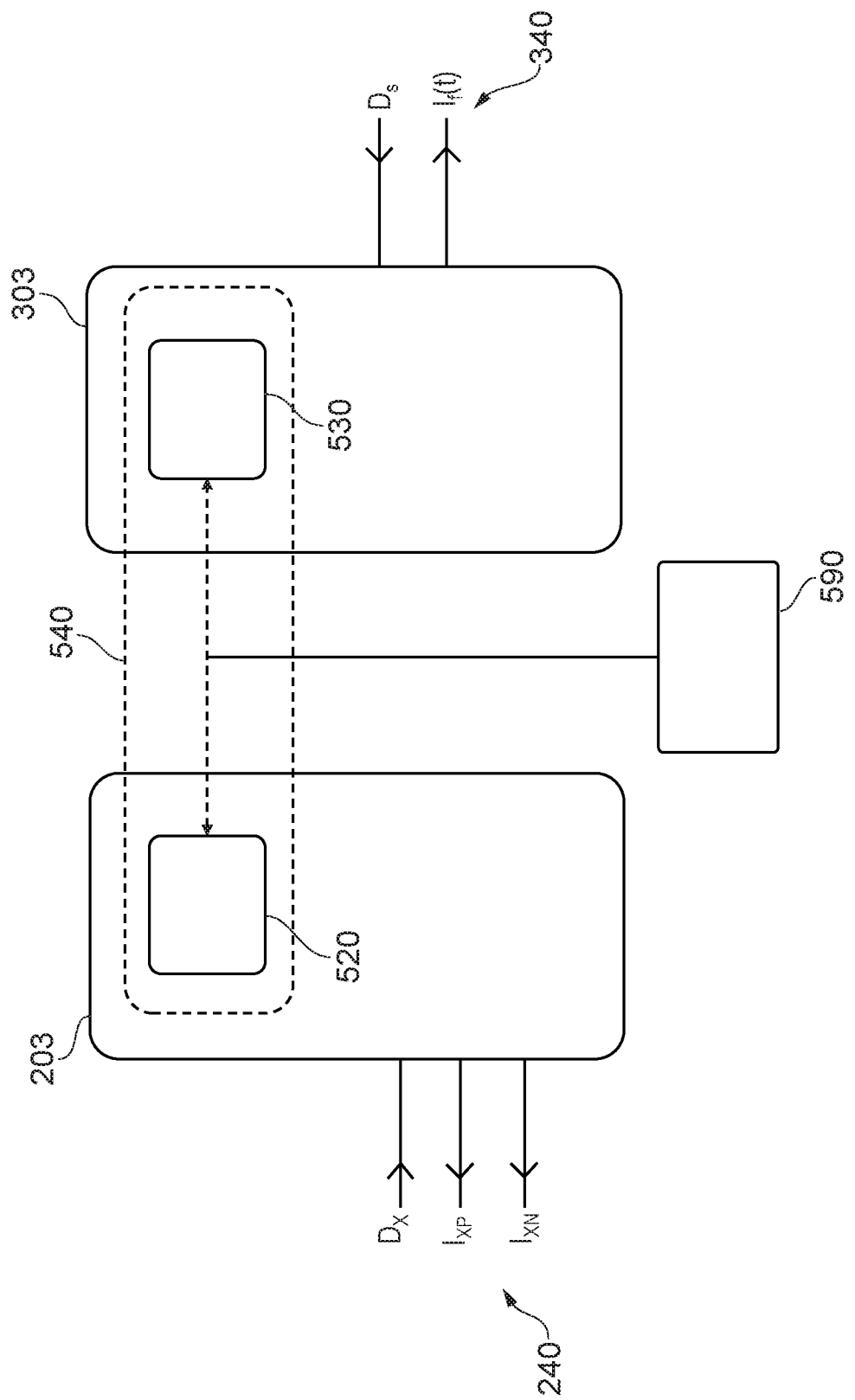
FIG. 5A shows a first mode of a noise-error reducing arrangement of the excitation DAC and the feedback DAC, according to an example of the present disclosure.

FIG. 5A shows an example view of the excitation DAC 203 and the feedback DAC 303 according to an example of the impedance measurement circuit 100 that is configured to ratiometrically cancel system gain errors. As shown in FIG. 5A, the excitation DAC 203 comprises a first hardware component 520 and the feedback DAC 303 comprises a second hardware component 530. The hardware component 520 may be any component of the excitation DAC 203 that exhibits an intrinsic noise power that contributes to errors in the system gain G as described above. For example, the hardware component 520 may be any n'th current source 222.n or the bias circuit 233 of the excitation DAC 203. Preferably, the hardware component 530 is a corresponding component of the feedback DAC 303 that performs a same or a corresponding function to the hardware component 520 in the feedback DAC 303. For example, if the hardware component 520 is a n'th current source 222.n of the excitation DAC 203, the hardware component 530 may be a m'th current source 322.m of the feedback DAC 303 such that n'th. Alternatively, if the hardware component 520 is the bias circuit 233 of the excitation DAC 203, the hardware component 530 may be the bias circuit 333 of the feedback DAC 303. Therefore, the hardware components 520 and 530 may be considered as a pair 540 of corresponding hardware components.

FIG. 5A illustrates a first mode of operation for the pair 540 of hardware components. In the first mode, the hardware component 520 is used in the excitation DAC 203. In particular, the hardware component 520 is used to perform operations in the excitation DAC 203 to convert instances of the digital input signal $D_X[p]$ to the analog output $I_X(t)$, as described above. For example, if the hardware component 520 is a n'th current source 222.n, the hardware component 520 supplies current to the current steering circuit 224.n and the current steering circuit 224.n operates as described above. If the hardware component 520 is the bias circuit 233, the hardware component 520 biases each current source 222.1 to 222.N of the excitation DAC.

Furthermore, the hardware component 530 is initially used in the feedback DAC 303 to perform operations to convert instances of the digital input $D_S[q]$ to the analog output $I_F(t)$, as described above. For example, if the hardware component 530 is a m'th current source 322.m, the hardware component 530 supplies current to the current steering circuit 324.m which operates as described above. If the hardware component 530 is the bias circuit 333, the hardware component 530 biases each current source 322.1 to 322.M of the feedback DAC.

As such, in the first mode shown in FIG. 5A, the hardware component 520 may contribute to an error in $I_{XDAC}$. The hardware component 530 may contribute to an error in $I_{ADC}$.

Figure 5B:
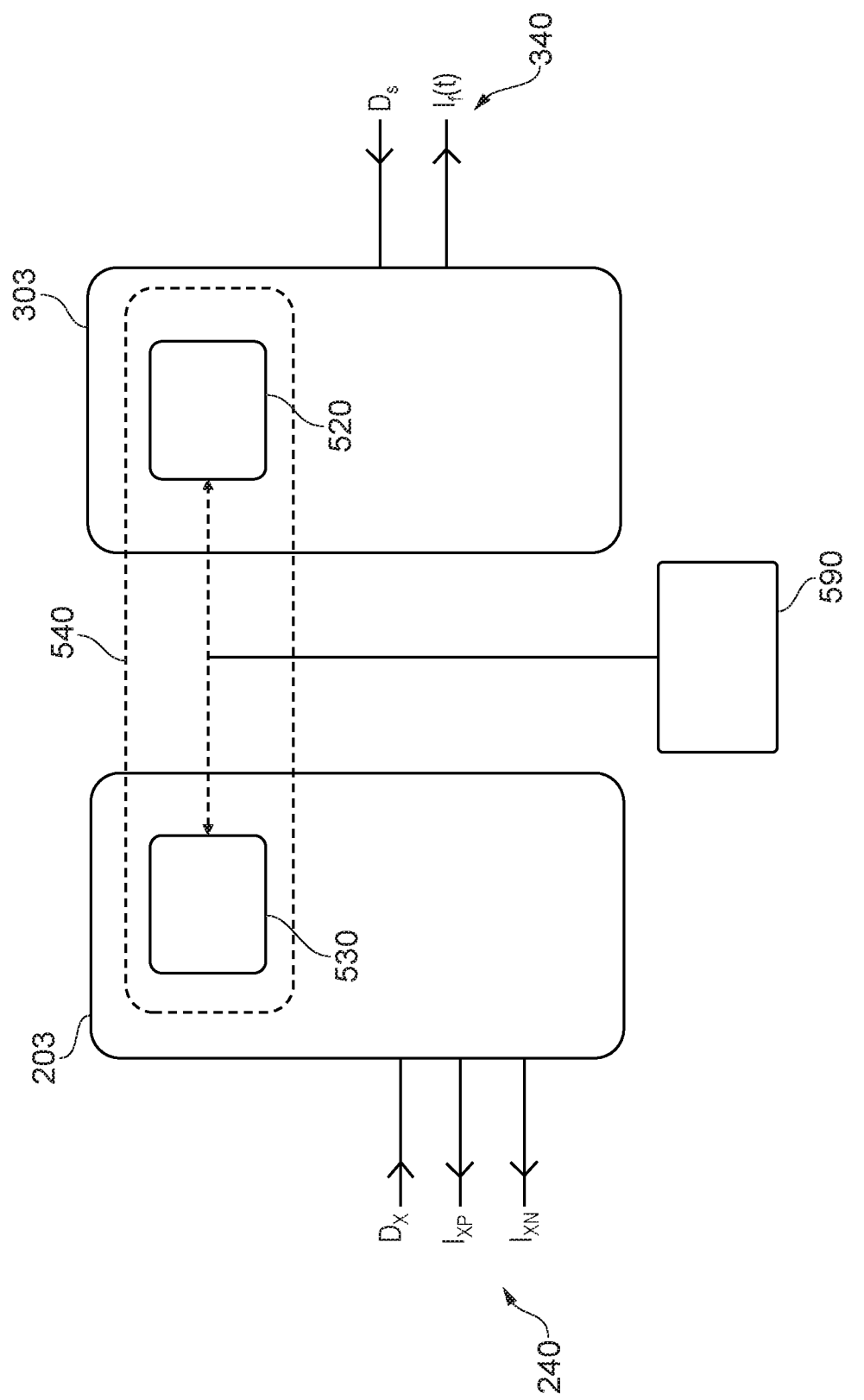
FIG. 5B shows a second mode of the noise-error reducing arrangement of the excitation DAC and the feedback DAC of FIG. 5A.

FIG. 5B shows a second mode of operation for the pair of hardware components 540. As shown in FIG. 5B, the hardware component 520 has been swapped with the hardware component 530. In particular, the hardware component 530 is now being used in the excitation DAC 203 to perform operations to convert instances of the digital input signal $D_X[p]$ to the analog output NO. For example, if the hardware component 530 was a m'th current source 322.m of the feedback DAC 303, the hardware component 530 now supplies current to the current steering circuit 224.n in the excitation DAC 203. If the hardware component 530 was the bias circuit 333, the hardware component 530 now biases each current source 222.1 to 222.N of the excitation DAC.

Furthermore, in FIG. 5B, the hardware component 520 is now being used in the feedback DAC 303 to perform operations to convert instances of the digital input $D_S[q]$ to the analog output $I_F(t)$. For example, if the hardware component 520 was a n'th current source 222.n of the excitation DAC 203, the hardware component 520 now supplies current to the current steering circuit 324.m of the feedback DAC 303. If the hardware component 520 was the bias circuit 233, the hardware component 520 now biases each current source 322.1 to 322.M of the excitation DAC.

As such, in the second mode, the hardware component 520 may now contribute to an error in $I_{ADC}$, and the hardware component 530 may now contribute to an error in $I_{XDAC}$.

By continuously alternating between the first and the second modes at an appropriate speed, the $I_{XDAC}$ will experience the same average error as the $I_{ADC}$ over a period of time. In particular, the errors caused by the first hardware component 520 will be equally spread between denominator and the numerator of the system gain G over time. Similarly, the errors caused by the second hardware component 530 will be equally spread between the denominator and the numerator of the system gain G over time. Therefore, the system gain G will effectively be stabilised against magnitude errors caused by both hardware components 520 and 530 of the pair 540 of hardware components.

The impedance measurement circuit 100 may be configured to use any appropriate means to switch the pair 540 of hardware components between the first and the second mode of operation. For example, as shown in FIGS. 5A and 5B, the impedance measurement circuit 100 may comprise a controller 590 arranged to control the swapping of the pair of hardware components 540 between excitation DAC 203 and the feedback DAC 303 in the first and the second mode of operation. In some examples, the controller 590 may switch the pair of hardware components 540 between the first and the second modes at a predetermined frequency. For example, the predetermined frequency may be equal to the clocking frequency of the excitation DAC and the feedback DAC, whereby the excitation DAC and the feedback DAC have the same clocking frequency ($1/T_S = 1/T_X$). In such an example, each DAC may convert one instance of the respective digital input in each mode of operation before changing to the next operating mode. Alternatively, the predetermined frequency may be a frequency that is lower than the clocking frequencies of the excitation DAC ($1/T_X$) and the feedback DAC ($1/T_S$). This may allow for multiple instances of the digital input to be converted between changes in the mode of operation. In such an example, the feedback DAC and the excitation DAC may or may not have equal clocking frequencies. In either case, the predetermined frequency may also be a frequency that is greater than the frequency $F_C$ of the magnitude error in the system gain G. More particularly, the predetermined frequency may be a frequency that is greater than twice the frequency $F_C$ of the magnitude error in the system gain G, so that fluctuations in the error are accounted for. In other examples, the controller 590 may switch the pair of hardware components 540 in a predetermined pattern or randomly. The optimal swapping frequency and/or swapping pattern for ratiometrically cancelling the gain errors may be determined through simulations and test data.

Figure 6:
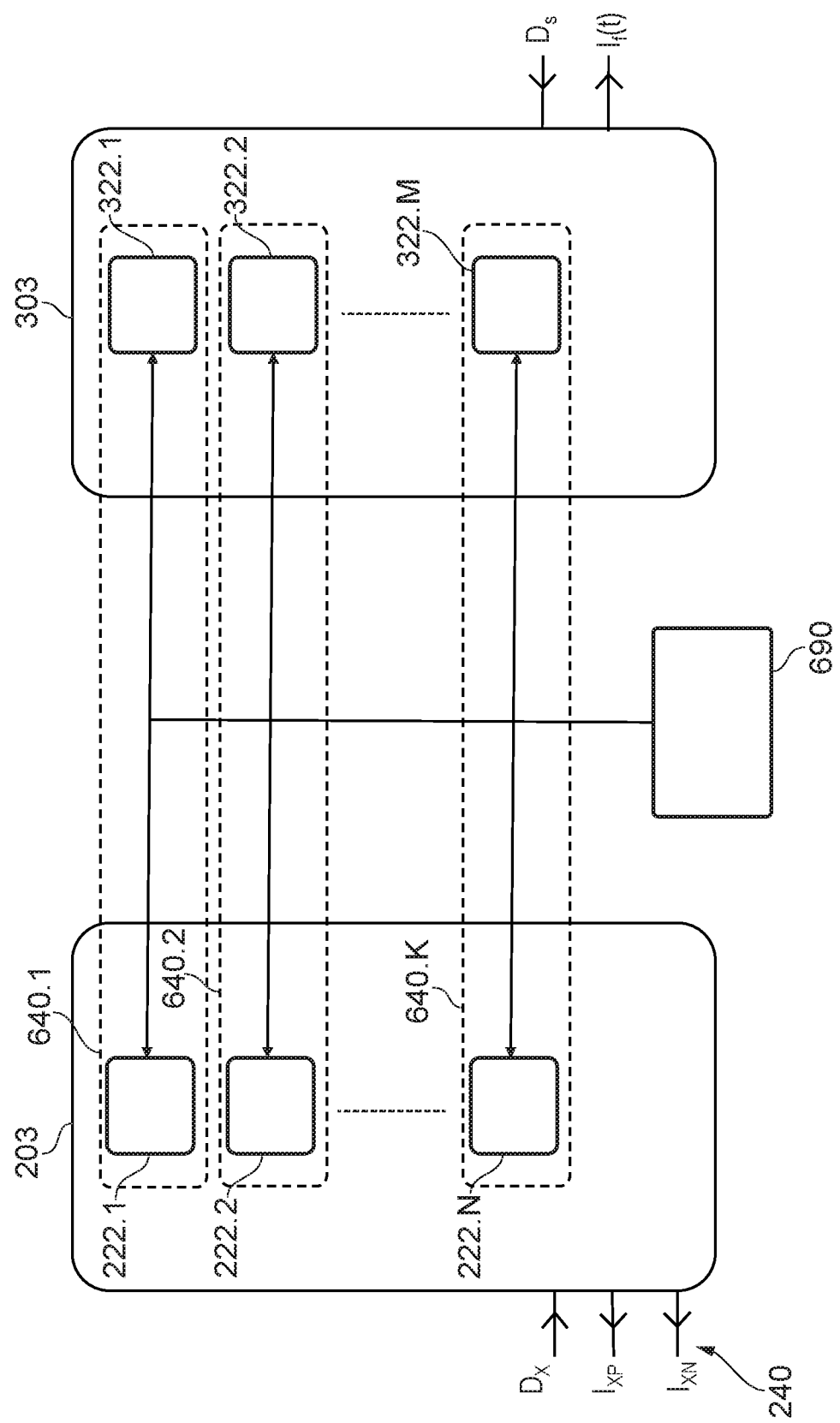
FIG. 6 shows a further example of a noise reducing-error arrangement of an excitation DAC and a feedback DAC, which involves swapping current sources of the excitation DAC with current sources of the feedback DAC.

The above technique can be extended to stabilise the system gain G against magnitude errors from multiple pairs of hardware components. For example, FIG. 6 shows an example view of the excitation DAC 203 and the feedback DAC 303 according to a further example of the impedance measurement circuit 100 that is configured to ratiometrically cancel system gain errors. As illustrated in FIG. 6A, the excitation DAC 203 initially comprises each current source 222.1 to 222.N. and the feedback DAC 303 initially comprises each current source 322.1 to 322.M. As illustrated, the current sources may be considered grouped in distinct pairs such that a pair 640.k comprises the current source 222.n and the current source 322.m, wherein k=1 ... K and k=n=m and K=N=M.

Each k'th pair of current sources 640.k is arranged to operate in a respective first mode and a second mode as described above in relation to FIGS. 5A and 5B. In particular, in the first mode for a pair 640.k, the current source 222.n is used in the excitation DAC 203 to perform operations in the excitation DAC 203 to convert instances of the digital input signal $D_X[p]$ to the analog output $I_X(t)$, as described above. For example, the current source 222.n supplies current to the current steering circuit 224.n and the current steering circuit 224.n operates as described above. Furthermore, the current source 322.m is used in the feedback DAC 303 to perform operations to convert instances of the digital input $D_S[q]$ to the analog output $I_F(t)$, as described above. For example, the current source 322.m supplies current to the current steering circuit 324.m which operates as described above. As such, in the first mode, the current source 222.n may contribute to an error in $I_{XDAC}$. The current source 322.m may contribute to an error in $I_{ADC}$.

In the second mode of operation for the pair 640.k, the current source 222.n will be swapped with the current source 322.m. In particular, current source 322.m will now supply current to the current steering circuit 224.n in the excitation DAC 203 instead of the current steering circuit 324.m. Furthermore, in the second mode, the current source 222.n will now be used to supply current to the current steering circuit 324.m of the feedback DAC 303 instead of the current steering circuit 224.n.

Each pair of current sources 640.k can be controlled to continuously switch between the respective first and second modes of operation, independently of the operating mode of the other pairs of current sources. For example, as shown in FIG. 6A, the impedance measurement circuit 100 may comprise a controller 690 configured to independently control the operating mode of each pair of current sources 640.1 to 640.K. This way, each pair of current sources 660.k can be switched between the first and second mode of operation based on their individual requirements for optimally stabilising the system gain G. In some examples, the controller 690 may switch each pair of current sources 660.k between the first and the second modes at a respective predetermined frequency, e.g. any predetermined frequency described above. In other examples, the controller 690 may switch the pairs of current sources 640.1 to 640.k between the first and second modes in a predetermined pattern or randomly. The optimal swapping frequencies and/or swapping patterns for ratiometrically cancelling the gain errors may be determined through simulations and test data.

Figure 7:
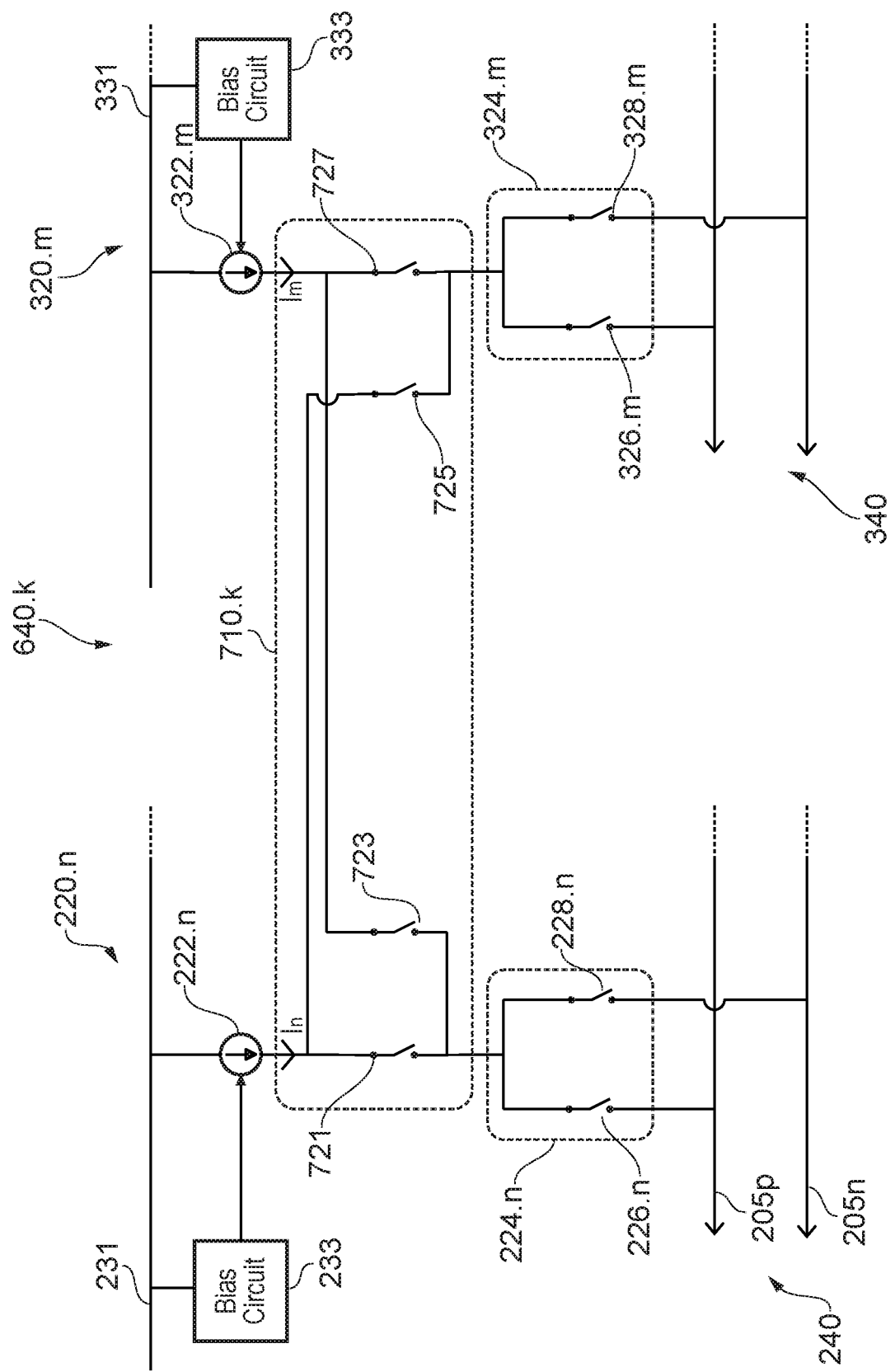
FIG. 7 shows an example implementation of the noise-error reducing arrangement of FIG. 6.

FIG. 7 illustrates an example current source switching arrangement by which a k'th pair of current sources 640.k may be operated in the first and the second mode as described above. In particular FIG. 7 shows an example arrangement of how a current source 222.n from a n'th DAC unit 220.n of the excitation DAC 203 may be swapped with a corresponding current source 322.m from a m'th DAC unit 320.m of the feedback DAC 303 as described above.

As shown in FIG. 7, the impedance measurement circuit 100 further comprises a switching network 710.k. The switching network 710.k comprises a plurality of switches 721.k, 723.k, 725.k and 727.k. The switch 721.k is arranged to switchably couple the output of the current source 222.n to the current steering circuit 224.n. The switch 723.k is arranged to switchably couple the output of the current source 322.m to the current steering circuit 224.n. The switch 725.k is arranged to switchably couple the output of the current source 222.n to the current steering circuit 324.m. The switch 727.k is arranged to switchably couple the output of the current source 322.m to the current steering circuit 324.m. As such, the switching network 710.k provides a plurality of switchable current paths from the current source 222.n to each of the current steering circuits 224.n and 324.m, and from the current source 322.m to each of the current steering circuits 224.n and 324.m. Moreover, the switching network 710.k, and each current steering circuit 224.n and 324.m together provides a plurality of switchable current paths from the current source 222.n to each DAC output 240 and 340, and from the current source 322.m to each DAC output 240 and 340.

In the first mode of operation, the switches 721.k and 727.k are closed, and the switches 723.k and 725.k are opened. The current source 222.n supplies the current $I_n$ to the current steering circuit 224.n of the excitation DAC 203 and the current source 322.m supplies the current $I_m$ to the current steering circuit 324.*m* of the feedback DAC 303. The current steering circuit 224.*n* may steer the current $I_n$ to either branch 205*p*/205*n* of the DAC output 240 depending on the value of the corresponding n'th bit of the digital input signal $D_X[p]''$, as described above in relation to FIG. 2B. Furthermore, the current steering circuit 324.*m* may steer the current $I_m$ to the DAC output 340 depending on the value of the corresponding m'th bit of the digital input signal $D_S[q]m$, as described above in relation to FIG. 3C. Whilst in the first mode, each DAC 203 and 303 may convert one or multiple instances of the respective digital input signals.

In the second mode of operation, the switches 721.*k* and 727.*k* are opened, and the switches 723.*k* and 725.*k* are closed. The current source 322.*m* supplies the current $I_m$ to the current steering circuit 224.*n* of the excitation DAC 203 and the current source 222.*n* supplies the current $I_n$ to the current steering circuit 324.*m* of the feedback DAC 303. Therefore, in the second mode, the current steering circuit 224.*n* instead steers the current $I_m$ to either branch 205*p*/205*n* of the DAC output 240 depending on the value of the corresponding n'th bit of the digital input signal $D_X[p]''$. Furthermore, the current steering circuit 324.*m* instead steers the current $I_n$ to the DAC output 340 depending on the value of the corresponding m'th bit of the digital input signal $D_S[q]'''$. Whilst in the second mode, each DAC 203 and 303 may convert one or multiple instances of the respective digital input signal.

Although not shown in FIG. 7, it will be appreciated that the states of the switches 721.*k*, 73.*k*, 725.*k* and 727.*k* may be controlled by the controller 690 shown in FIG. 6 in order to transition the pair of current sources 640.*k* between the first and the second mode of operation. Furthermore, it will also be appreciated that the impedance measurement circuit 100 may comprise a total of K switching networks similar to the switching network 710.*k* shown in FIG. 7, in order to independently transition each of the pairs of current sources 640.1 to 640.K between the first and second modes as described in relation to FIG. 6.

Figure 8:
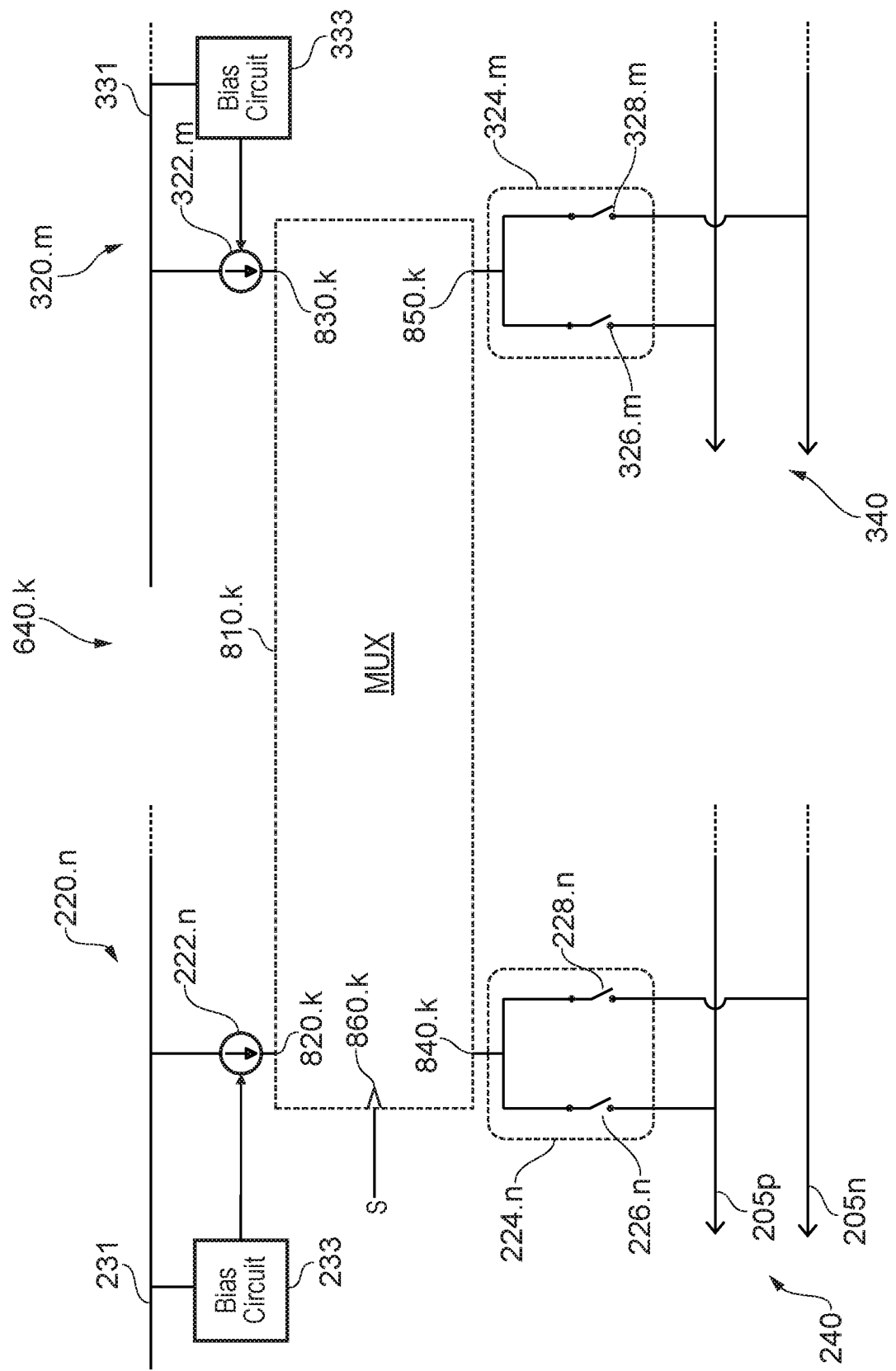
FIG. 8 shows an alternative example implementation of the noise-error reducing arrangement of FIG. 6.

FIG. 8 shows an alternative current source switching arrangement to the arrangement of FIG. 7. As shown in FIG. 8, the switching network 710.*k* may be replaced by a multiplexer 810.*k*. The multiplexer comprises a first input 820.*k* coupled to an output of the current source 222.*n*, a second input 830.*k* coupled to an output of the current source 322.*m*, a first output 840.*k* coupled to the input to the current steering circuit 224.*n* and a second output 850.*k* coupled to the input to the current steering circuit 324.*m*. The multiplexer 810.*k* also comprises a selection input 860.*k* configured to receive a control signal "S.k".

In the first mode (e.g. when S.k=1 or high), the multiplexer 810.*k* couples the first input 820.*k* to the first output 840.*k*, and the second input 830.*k* to the second output 850.*k*. As such, in the first mode the output of the current source 222.*n* will be routed or coupled to the input to the current steering circuit 224.*n* and the current source 322.*m* will be routed or coupled to the input to the current steering circuit 324.*m*. Therefore, the current steering circuit 224.*n* can steer the current $I_n$ to either branch 205*p*/205*n* of the DAC output 240 depending on the value of the corresponding n'th bit of the digital input signal $D_X[p]''$, as described above. Furthermore, the current steering circuit 324.*m* can steer the current $I_m$ to the DAC output 340 depending on the value of the corresponding m'th bit of the digital input signal $D_S[q]'''$, also as described above.

In the second mode (e.g. when S.k=0 or low), the multiplexer 810.*k* couples the first input 820.*k* to the second output 850.*k*, and the second input 830.*k* to the first output 840.*k*. As such, in the second mode the output of the current source 222.*n* will be routed or coupled to the input to the current steering circuit 324.*m* and the current source 322.*m* will be routed or coupled to the input to the current steering circuit 224.*n*. Therefore, in the second mode, the current steering circuit 224.*n* instead steers the current $I_m$ to either branch 205*p*/205*n* of the DAC output 240 depending on the value of the corresponding n'th bit of the digital input signal $D_X[p]''$. Furthermore, the current steering circuit 324.*m* instead steers the current $I_n$ to the DAC output 340 depending on the value of the corresponding m'th bit of the digital input signal $D_S[q]'''$.

Although not shown in FIG. 8, it will be appreciated that the control signal S.k may be supplied by the controller 690 shown in FIG. 6 in order to transition the pair of current sources 640.*k* between the first and the second mode of operation. Furthermore, it will also be appreciated that the impedance measurement circuit 100 may comprise a total of K multiplexers similar to the multiplexer 810.*k* shown in FIG. 8, in order to transition each of the pairs of current sources 640.1 to 640.K between the first and second modes as described in relation to FIG. 6. However, other arrangements are possible. For example, the impedance measurement circuit 100 may instead comprise one multiplexer that is configured to perform the operations of each of the multiplexers 810.1 and 810.K.

In most circumstances, swapping the current sources of the excitation and feedback DACs as described above can be sufficient for stabilising the system gain G in view of both the current source noise and the bias circuit noise. For example, by using a current source 222.*n* of the excitation DAC in the feedback DAC, the noise of the bias circuit 233 that is biasing the current source 222.*n* will have an effect in the feedback DAC and therefore affect the full scale current $I_{ADC}$ of the ADC 315. However, it can still be advantageous to swap the bias circuits 233 and 333 of the excitation and feedback DACs independently of their current sources, for a further degree of control over the system gain G.

Figure 9:
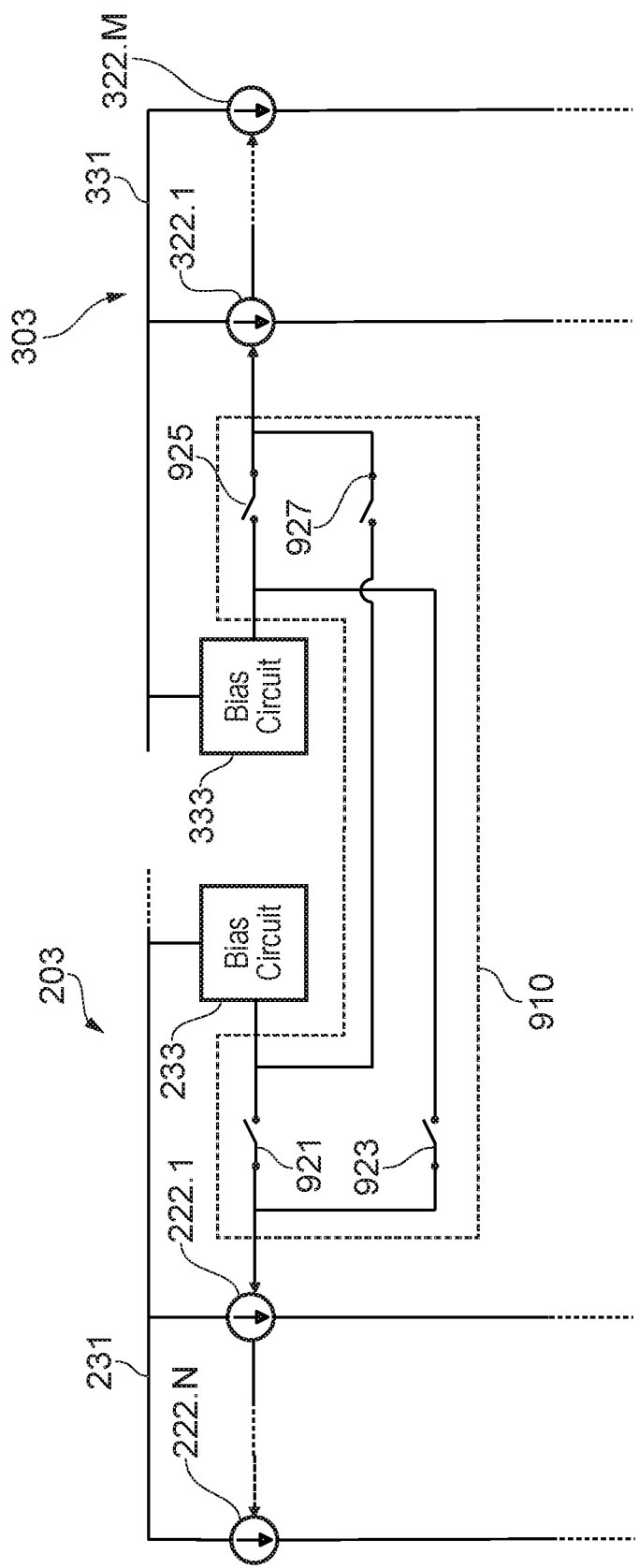
FIG. 9 shows an example implementation of the noise-error reducing arrangement of FIG. 5, which involves swapping a bias circuit of the excitation DAC with a bias circuit of the feedback DAC.

FIG. 9 shows an example bias switching arrangement for swapping the bias circuit 233 of the excitation DAC 203 and the bias circuit 333 of the feedback DAC 303, as described above in relation to FIGS. 5A and 56. As shown in FIG. 9, the impedance measurement circuit 100 may comprise a bias switching network 910 coupled to both the excitation DAC 203 and the feedback DAC 303.

The bias switching network 910 comprises a plurality of switches 921, 923, 925 and 927. The switch 921 is arranged to switchably couple the bias circuit 233 to each of the current sources 222.1 to 222.N of the excitation DAC 203. The switch 923 is arranged to switchably couple the bias circuit 333 to each of the current sources 222.1 to 222.N of the excitation DAC 203. The switch 925 is arranged to switchably couple the bias circuit 333 to each of the current sources 322.1 to 322.M of the feedback DAC 303. The switch 927 is arranged to switchably couple the bias circuit 233 to each of the current sources 322.1 to 322.M of the feedback DAC 303.

In a first mode of operation of the bias switching network 910, the switches 921 and 925 are closed, and the switches 923 and 927 are opened. The bias circuit 233 biases each of the current sources 222.1 to 222.N of the excitation DAC 203 and the bias circuit 333 biases each of the current sources 322.1 to 322.M of the feedback DAC 303 as previously described. Whilst in the first mode, each DAC 203 and 303 may convert one or multiple instances of the respective digital input signals.

In the second mode of operation, the switches 921 and 925 are opened, and the switches 923 and 927 are closed. The bias circuit 333 now biases each of the current sources 222.1 to 222.N of the excitation DAC 203 and the bias circuit 233 now biases each of the current sources 322.1 to 322.M of the feedback DAC 303. Whilst in the second mode, each DAC 203 and 303 may convert one or multiple instances of the respective digital input signal.

Although not shown in FIG. 9, it will be appreciated that the states of the switches 921, 923, 925 and 927 may be controlled by a controller as described above in order to transition the bias circuits between the first and the second mode of operation. It should be appreciated that the impedance measurement circuit 100 may include and use the bias switching arrangement shown in FIG. 9 in conjunction with the current source switching arrangements shown in FIGS. 6 to 8. In this case, the controller may be configured to control the operating mode of the bias switching network 910 independently of the operating modes of the pairs of current sources 610.1 to 610.K. However, in other examples, the impedance measurement circuit 100 can implement the bias switching arrangement of FIG. 9 without a current source switching arrangement. In other examples, the impedance measurement circuit 100 may implement the current source switching arrangement without the bias switching arrangement.

In the above examples, it is described and illustrated that the excitation DAC 203 and the feedback DAC 303 comprise their own respective bias circuits 233 and 333. However, in some examples, the excitation DAC 203 and the feedback DAC 303 may share the same bias circuit.

Figure 10:
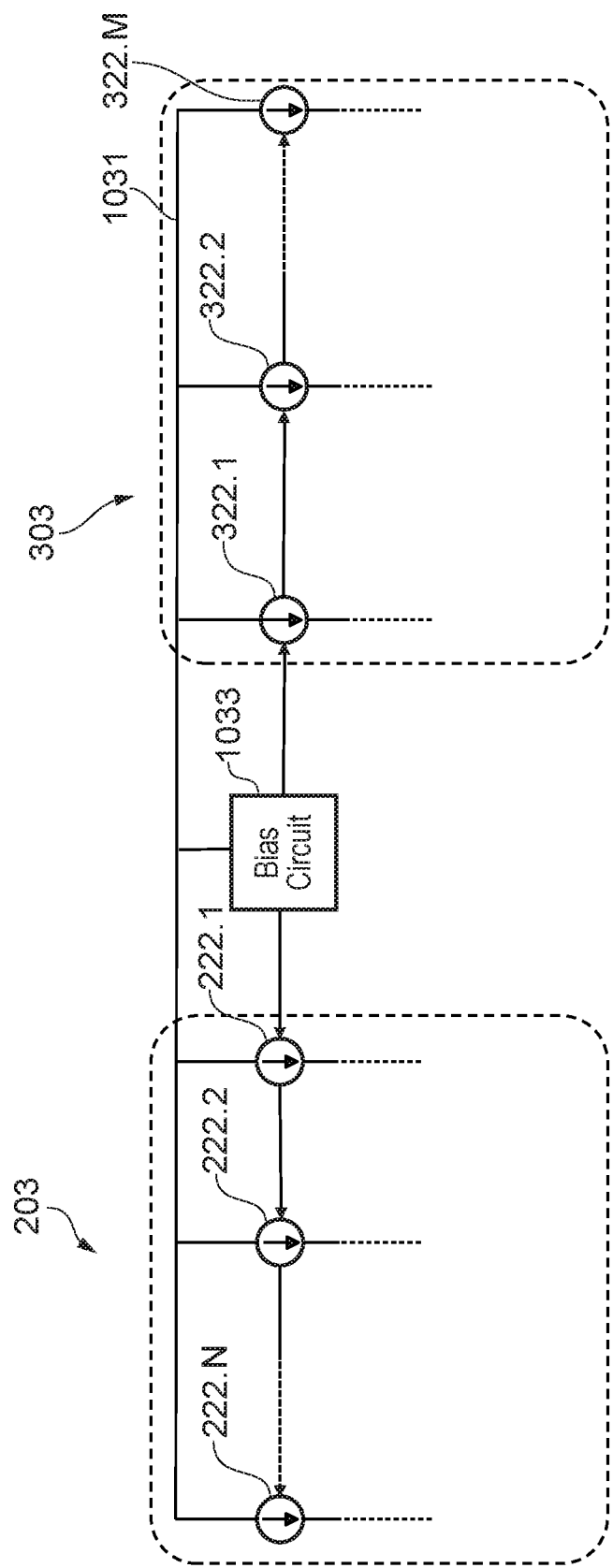
FIG. 10 shows a noise-error reducing arrangement of an excitation DAC and a feedback DAC according to a further example of the present disclosure, which involves sharing a bias circuit between the excitation DAC and the feedback DAC.

FIG. 10 illustrates a further example arrangement of the excitation DAC 203 and the feedback DAC 303 of the impedance measurement circuit 100. As shown, the impedance measurement circuit 100 may comprise a bias circuit 1033 coupled to a power supply rail 1031. Furthermore, the bias circuit 1033 is coupled to each of the current sources 222.1 to 222.N of the excitation DAC 203 and each of the current sources 322.1 to 322.M of the feedback DAC 303. As such, the bias circuit 1033 is configured to bias each of those current sources of the excitation DAC 203 and the feedback DAC 303.

In an example implementation of the arrangement of FIG. 10, the bias circuit 1033 may comprise a MOS transistor in a diode arrangement as described above with respect to FIG. 4. The gate terminal of the bias transistor may be coupled to the gate terminals of MOS transistors in each of the current sources 222.1 to 222.N and 322.1 to 322.M. As such, each current source 222.1 to 222.N and 322.1 to 322.M may be biased to output substantially the same current.

Advantageously, by sharing one bias circuit 1033 between the excitation DAC 203 and the feedback DAC 303, the effects of intrinsic noise from the bias circuit is significantly reduced in comparison to having a bias circuit for each DAC. This may further improve the stability of the system gain G.

As will be appreciated, the bias circuit arrangement of FIG. 10 may be implemented in the impedance measurement circuit 100 in combination with any of the current source switching arrangements of FIGS. 6 to 8. However, with the bias circuit arrangement of FIG. 10, it is not be necessary to implement the bias switching arrangement of FIG. 9 in the impedance measurement circuit 100. In other examples, the bias circuit arrangement of FIG. 10 may be implemented in the impedance measurement circuit 100 without a current source switching arrangement, which may still result in a more stabilised system gain G in comparison to the DAC arrangements of FIGS. 2B and 3C.

Figure 11:
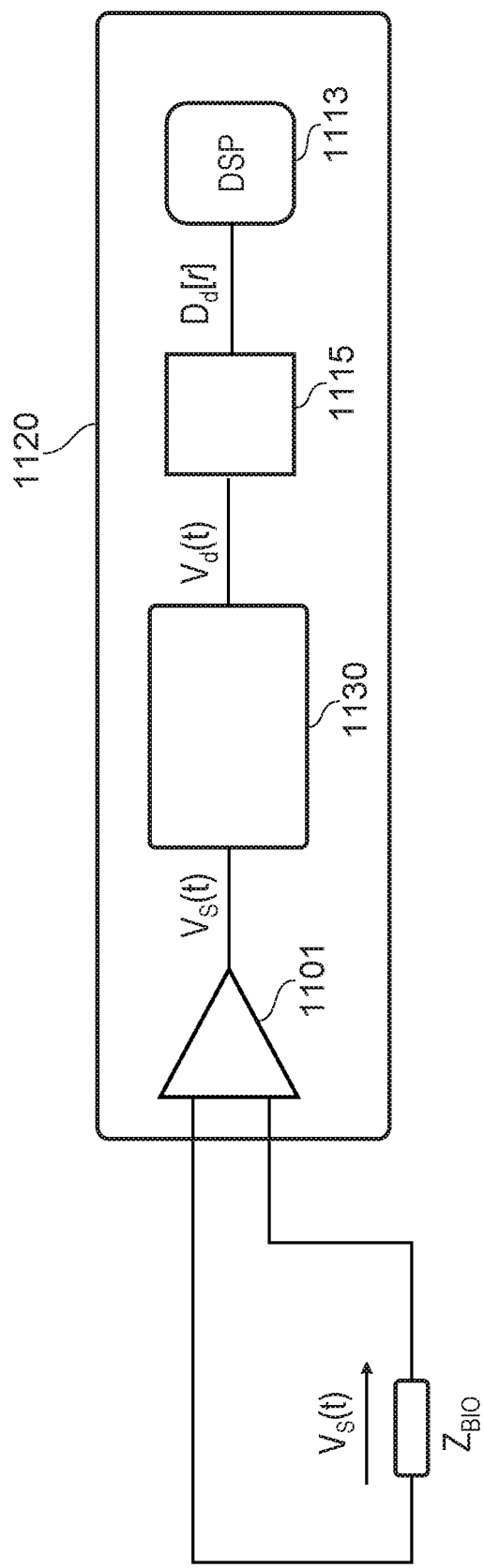
FIG. 11 shows an alternative example of a sensing circuit according to an example of the present disclosure.

In some implementations of the impedance measurement circuit 100, the sensing circuit 120 may demodulate the voltage signal $V_S(t)$ in the analog domain before converting it to a digital signal for the DSP. For example, FIG. 11 shows an alternative sensing circuit 1120 that comprises an input buffer 1101, an analog demodulator 1130, an analog to digital converter (ADC) 1115 and a digital signal processor (DSP) 1113. The input buffer 1101 is arranged to receive the voltage signal $V_S(t)$ and provide the voltage signal $V_S(t)$ to the demodulator 1130. The demodulator 1130 is configured to demodulate the voltage signal $V_S(t)$ in the analog domain in order to remove the carrier frequency component $F_C$ from the voltage signal $V_S(t)$. The demodulator 1130 outputs a corresponding demodulated signal $V_d(t)$ which may contain frequency components at $-F_{BIO}$ and $+F_{BIO}$. The ADC 1115 is configured to convert the demodulated voltage signal $V_d(t)$ into a digital representation of the demodulated voltage signal, denoted as $D_d[r]$. The ADC 1115 is arranged to output the digital signal $D_d[r]$ to the DSP 1113. The DSP 1113 is configured to analyse the digital signal $D_d[q]$ to detect variations in the bioimpedance $Z_{BIO}$. For example, the DSP 1113 may be configured to detect the frequency of interest $F_{BIO}$, as explained above.

In the arrangement of FIG. 11, the demodulator 1130 may comprise a reference DAC for generating a reference voltage. The reference DAC may have a similar structure to the excitation DAC described above. Moreover, the excitation DAC 203 and the reference DAC may together exhibit intrinsic noise properties that cause magnitude errors in the signal Dd[r] and therefore inaccurate measurements of the bioimpedance $Z_{BIO}$. As such, the above techniques described in relation to the excitation DAC 203 and the feedback DAC 303, may also be applied between the excitation DAC 203 and the reference DAC in order to ratiometrically cancel errors in the digital signal Dd[r] when an analog demodulator 1130 is used.

Figure 12:
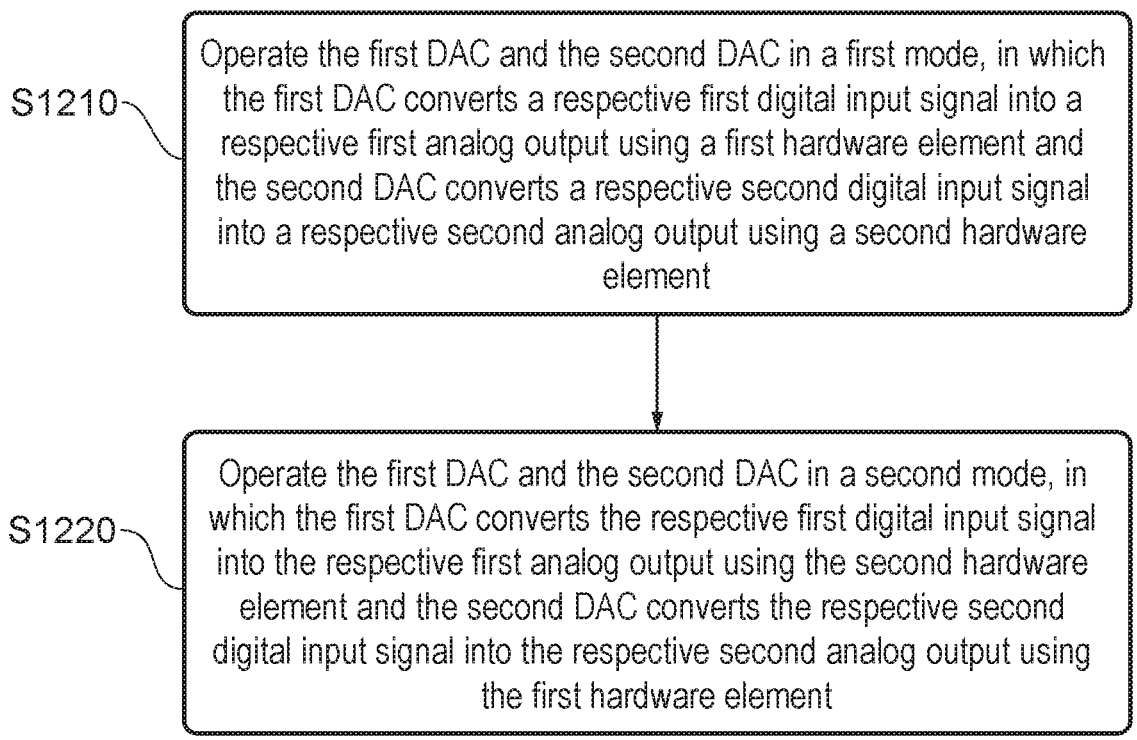
FIG. 12 shows a flow diagram illustrating a method of operating an impedance measurement circuit in accordance with an example of the present disclosure.

FIG. 12 shows a method of operating an impedance measurement circuit comprising a first DAC and a second DAC according to the examples of the present disclosure. In particular, the method illustrated in FIG. 12 may be understood as a method of operating the impedance measurement circuit 100 illustrated in FIGS. 1-11 using the techniques disclosed herein. In some examples, the first DAC may be the excitation DAC 203 and the second DAC may be the feedback DAC 303. In other examples, the second DAC may be the reference DAC shown in FIG. 11.

At step S1210, the first DAC and the second DAC operate in a first mode of operation. In the first mode, the first DAC converts its respective digital input signal into its analog output using a first hardware circuit element. For example if the first DAC is the excitation DAC 203, the first DAC converts the digital input signal $D_X[p]$ into its analog output $I_X(t)$ using the first hardware circuit element. Furthermore, in the first mode, the second DAC converts its respective digital input signal into its respective analog output using a second hardware circuit element. For example, if the second DAC is the feedback DAC 303, the second DAC converts its respective digital input $D_S[q]$ into its respective analog output $I_F(t)$ using the second hardware circuit element. As described above, according to some examples, the first hardware circuit element may be a current source 222.n of the excitation DAC 203 and the second hardware circuit element may be a corresponding current source 322.m of the feedback DAC 303. Alternatively or additionally, the first hardware circuit element may be a bias circuit 233 of the excitation DAC 203 and the second hardware circuit element may be a bias circuit 333 of the feedback DAC 303.

At step S1220, the first DAC and the second DAC operate in a second mode of operation. In the second mode, the first DAC now converts its respective digital input signal into its analog output using the second hardware circuit element. For example, if the first DAC is the excitation DAC 203, the first DAC now converts its respective digital input signal $D_X[p]$ into its analog output $I_X(t)$ using the second hardware circuit element. Furthermore, in the second mode, the second DAC now converts its respective digital input into its respective analog output using the first hardware circuit element. For example, if the second DAC is the feedback DAC 303, the second DAC now converts its respective digital input $D_S[q]$ into its respective analog output $I_F(t)$ using the first hardware circuit element. In other words, the first hardware circuit element and the second hardware circuit element are effectively swapped between the first DAC and the second DAC.

It should be appreciated that any of the above techniques and examples may be used to swap the first hardware circuit element and the second hardware circuit element in accordance with the present method. For example, if the first hardware circuit element is a current source first DAC and the second hardware circuit element is a corresponding current source of the feedback DAC, any of the techniques and circuit arrangements described in relation to those shown in FIGS. 5 to 8 may be used. Alternatively or additionally, if the first hardware circuit element is a bias circuit of the first DAC and the second hardware circuit element is a bias circuit of the second DAC, any of the techniques and circuit arrangements described in relation to those shown in FIGS. 5 and 9 may be used. Alternatively, in some examples of the present method, the first and second DACs may share a bias circuit as described in relation to FIG. 10.

In some examples, the method illustrated in FIG. 12 may further comprise alternating between the first and the second modes of operation. In some examples, the method may comprise alternating between the first and the second modes at a predetermined frequency. For example, the predetermined frequency may be equal to the clocking frequency of the excitation DAC and the feedback DAC, whereby the excitation DAC and the feedback DAC have the same clocking frequency ($1/T_S=1/T_X$). In such example, each DAC may convert one instance of the respective digital input in each mode of operation before changing to the next operating mode. Alternatively, the predetermined frequency may be a frequency that is lower than the clocking frequencies of the first DAC and the second DAC, to allow for multiple instances of the digital input to be converted between changes in the modes of operation. In such an example, the feedback DAC and the excitation DAC may or may not have equal clocking frequencies. In either case, the predetermined frequency may also be a frequency that is greater than the frequency $F_G$ of the magnitude error in the system gain G. More particularly, the predetermined frequency may be a frequency that is greater than twice the frequency $F_G$ of the magnitude error in the system gain G of the impedance measurement circuit 100, so that fluctuations in the error are accounted for. In other examples, the first and second modes may alternate in a predetermined pattern or randomly. The optimal swapping frequency and/or swapping pattern for ratiometrically cancelling the gain errors may be determined through simulations and test data.

Further Variations and Examples

In the above examples it is described that the bioimpedance $Z_{BIO}$ may be a thoracic impedance, and impedance measurement circuit 100 may be used to measure variations in the thoracic impedance at a low frequency $F_{BIO}=0.3$ Hz. However, it will be appreciated that the above techniques may be applied in any scenario that requires an impedance measurement circuit to detect and analyse slow variations in an impedance. For example, the impedance measurement circuit 100 may be used in lung wetness analysis, impedance tomography techniques for bladder, lung or throat mapping, skin impedance analysis, and/or sweat analysis. Furthermore, the impedance measurement circuit 100 be used for analysing non-clinical impedances, such as in electrical impedance spectroscopy for gas or sample analysis, and for measuring battery health.

In the above disclosures, there are described preferred examples of the ADC 315, feedback DAC 303, excitation DAC 203, and preferred examples of which hardware components of the feedback DAC 303 and excitation DAC 203 are swapped according to the techniques of the present disclosure. It will however be appreciated that the techniques of the present disclosure can be used with any type of impedance measurement circuit that comprises an excitation DAC, and an ADC comprising a DAC (e.g. a feedback DAC) that has a similar or corresponding structure or architecture to the excitation DAC.

For example, it is explained above that the ADC 315 is preferably a continuous time sigma delta ADC. In other examples, the ADC 315 may be a successive approximation register (SAR) ADC. The SAR ADC may comprise a DAC, such as a feedback DAC arranged in a feedback loop of the SAR ADC, which is similar or corresponding in structure or architecture to the excitation DAC 203 as explained above. Hardware circuit elements of the feedback DAC of the SAR ADC may be swapped with corresponding hardware circuit elements of the excitation DAC 203 as described herein.

In other examples of the impedance measurement circuit, the ADC may be a discrete time sigma-delta ADC comprising a feedback DAC that is similar or corresponding in structure or architecture to the excitation DAC 203. Hardware circuit elements of the feedback DAC of the discrete time sigma delta ADC may be swapped with corresponding hardware circuit elements of the excitation DAC 203 as described herein.

It is further described above that the feedback DAC 303 and excitation DAC 203 are preferably current steering DACs. In such DACs, the current sources and/or bias circuits of the DACs may exhibit intrinsic noise that contributes to the system gain errors, in which case it may be preferred to swap at least current sources and/or bias circuits of the feedback DAC 303 with corresponding current sources and/or bias circuits of the excitation DAC 203 in order to ratiometrically cancel the system gain error.

In other examples, the feedback DAC 303 and the excitation DAC 203 may comprise other components that contribute to the system gain error. In some examples, each DAC may comprise one or more resistors. As one particular example, the DACs may comprise a network of resistors, such as a R-2R ladder network. The resistors in each DAC may also exhibit intrinsic noise and therefore contribute to time varying errors in the system gain. As such, the techniques disclosed herein can also be used to swap one or more resistors of the feedback DAC 303 with one or more resistors of the excitation DAC 203. For example, with reference to the discussion of FIGS. 5A and 5B, the hardware component 520 may be considered a resistor of the excitation DAC 203. The hardware component 530 may be considered a corresponding resistor of the feedback DAC 303. In a particular example, if the resistor of the excitation DAC 203 is associated with a particular n'th bit or unit of the excitation DAC 203, the resistor of the feedback DAC may be associated with a corresponding m'th bit or unit of the feedback DAC 303.

In other examples, each DAC may comprise one or more capacitors. As one particular example, the DACs may comprise a network of capacitors, such as a switched capacitor network. The capacitors in each DAC may also exhibit intrinsic noise and therefore contribute to time varying errors in the system gain, or otherwise benefit from swapping. As such, the techniques disclosed herein can also be used to swap one or more capacitors of the feedback DAC 303 with one or more capacitors of the excitation DAC. For example, with reference to the discussion of FIGS. 5A and 5B, the hardware component 520 may be a capacitor of the excitation DAC 203. The hardware component 530 may be a corresponding capacitor of the feedback DAC 303. In a particular example, if the capacitor of the excitation DAC 203 is associated with a particular n'th bit or unit of the excitation DAC 203, the capacitor of the feedback DAC may be associated with a corresponding m'th bit or unit of the feedback DAC 303.

As is clear from the above, the hardware component 520 may be any hardware component of the excitation DAC 203 (e.g. a resistor, capacitor, current source or bias circuit), and the hardware component 530 may be any corresponding hardware component of the feedback DAC (e.g. a resistor, capacitor, current source, or bias circuit) that may benefit from swapping using the techniques described herein.

The invention claimed is:

1. An impedance measurement apparatus comprising:
a first hardware circuit element and a second hardware circuit element;
a first digital to analog converter DAC arranged to convert a first digital input to a first output signal using the first or the second hardware circuit elements; and
a second DAC arranged to convert a second digital input to a second output signal using the first or the second hardware circuit elements,
wherein the apparatus is configured to operate in:
a first mode in which the first DAC converts the first digital input using the first hardware circuit element and the second DAC converts the second digital input using the second hardware circuit element, and
a second mode in which the first DAC converts the first digital input using the second hardware circuit element and the second DAC converts the second digital input using the first hardware circuit element.

2. The apparatus of claim 1, wherein the apparatus is configured to alternate between the first mode and the second mode.

3. The apparatus of claim 2, wherein the apparatus is configured to alternate between the first mode and the second mode independently of the first and second digital inputs.

4. The apparatus of claim 3, wherein the apparatus is configured to alternate between the first and second modes randomly or in a predetermined pattern.

5. The apparatus of claim 1, wherein the first hardware circuit element and the second hardware circuit element are of the same type.

6. The apparatus of claim 1, wherein the first hardware circuit element is a first current source, and the second hardware circuit element is a second current source.

7. The apparatus of claim 6, wherein the first DAC is configured to steer current from the first or the second current source to a first DAC output depending on the first digital input, and wherein the second DAC is configured to steer current from the first or the second current source to a second DAC output depending on the second digital input.

8. The apparatus of claim 6, further comprising a plurality of switchable paths arranged to: in the first mode, supply current from the first current source to the first DAC and from the second current source to the second DAC; and in the second mode, supply current from the second current source to the first DAC and from the first current source to the second DAC.

9. The apparatus of claim 6, further comprising a biasing circuit configured to bias the first and the second current sources.

10. The apparatus of claim 1,
wherein the first hardware circuit element is a first bias circuit arranged to bias a first current source of the first DAC or a second current source of the second DAC, and the second hardware circuit element is a second bias circuit arranged to bias the first current source or the second current source.

11. The apparatus of claim 10, wherein the apparatus is configured such that:
in the first mode, the first bias circuit biases the first current source and the second bias circuit biases the second current source; and
in the second mode, the first bias circuit biases the second current source and the second bias circuit biases the first current source.

12. The apparatus of claim 1, further comprising:
an excitation circuit for outputting an excitation signal to an impedance under measurement, the excitation circuit comprising the first DAC; and
a sensing circuit arranged to sense a signal across the impedance, the sensing circuit comprising the second DAC.

13. A method of ratiometrically cancelling gain errors in an impedance measurement apparatus having a first digital to analog converter DAC and a second DAC, comprising:
operating the first DAC and the second DAC in a first mode, in which the first DAC converts a first digital input to a respective first output signal using a first hardware circuit element, and the second DAC converts a second digital input to a second output signal using a second hardware circuit element;
operating the first DAC and the second DAC in a second mode in which the first DAC converts the first digital input to the respective first output signal using the second hardware circuit element, and the second DAC converts the second digital input to the second output signal using the first hardware circuit element.

14. The method of claim 13, further comprising alternating between the first and second modes of operation.

15. The method of claim 14, wherein the first and second modes alternate independently of the digital inputs.

16. The method of any of claim 13, comprising alternating between the first and second modes randomly or in a predetermined pattern.

17. The method of claim 13, wherein the first hardware circuit element is a first current source, and the second hardware circuit element is a second current source, and wherein:
in the first mode the first DAC converts the first digital input by steering current from the first current source to a first DAC output depending on the first digital input, and the second DAC converts the second digital input by steering current from the second current source to a second DAC output depending on the second digital input; and in the second mode the first DAC converts the first digital input by steering current from the second current source to a first DAC output depending on the first digital input, and the second DAC converts the second digital input by steering current from the first current source to a second DAC output depending on the second digital input.

18. The method of claim 13, wherein the first hardware circuit element is a first bias circuit, and the second hardware circuit element is a second bias circuit, wherein:

in the first mode the first DAC converts the first digital input using a current source biased by the first bias circuit, and the second DAC converts the second digital input using a current source biased by the second bias circuit; and in the second mode the first DAC converts the first digital input using a current source biased by the second bias circuit, and the second DAC converts the second digital input using a current source biased by the first bias circuit.

19. The method of claim 13, wherein the first DAC is comprised in an excitation circuit for outputting an excitation signal to a bioimpedance, and the second DAC is in a sensing circuit arranged to sense a signal across a bioimpedance.

20. An impedance measurement apparatus comprising:

a first digital to analog converter DAC comprising a first output, wherein the first DAC is configured to convert a first digital input to a first output signal by steering current from a first current source to the first output based on the first digital input, a second DAC comprising a second output, the second DAC configured to convert a second digital input to a second output signal by steering current from a second current source to the second output based on the second digital input, and a bias circuit configured to bias the first and the second current source.

* * * * *

UNITED STATES PATENT AND TRADEMARK OFFICE
CERTIFICATE OF CORRECTION

| | |
|---|---|
| PATENT NO. | : 11,272,854 B1 |
| APPLICATION NO. | : 17/010185 |
| DATED | : March 15, 2022 |
| INVENTOR(S) | : Tansley et al. |

It is certified that error appears in the above-identified patent and that said Letters Patent is hereby corrected as shown below:

On the Title Page

Item [22], Column 1, Line 1, after "2020", insert --¶(65) Prior Publication Data
US 2022/0061690 A1 Mar. 03, 2022--

In the Claims

Column 23, Line 34, Claim 1, delete "DAC" and insert --(DAC)-- therefor

Column 24, Line 40, Claim 13, delete "DAC" and insert --(DAC)-- therefor

Column 24, Line 57, Claim 16, after "of", delete "any of"

Column 26, Line 10, Claim 20, delete "DAC" and insert --(DAC)-- therefor

Page 1 of 1

Signed and Sealed this
Tenth Day of May, 2022

Katherine Kelly Vidal
*Director of the United States Patent and Trademark Office*